US010058853B2

(12) United States Patent
Lai et al.

(10) Patent No.: US 10,058,853 B2
(45) Date of Patent: *Aug. 28, 2018

(54) CATALYST COMPOSITIONS AND USE IN HEAVY AROMATICS CONVERSION PROCESSES

(71) Applicant: ExxonMobil Chemical Patents Inc., Baytown, TX (US)

(72) Inventors: Wenyih F. Lai, Bridgewater, NJ (US); Christine N. Elia, Bridgewater, NJ (US); Jane C. Cheng, Bethlehem, PA (US); Shifang L. Luo, Annandale, NJ (US); Hari Nair, Somerville, NJ (US); Joshua I. Cutler, Somerville, NJ (US); Doron Levin, Highland Park, NJ (US); Chuansheng Bai, Phillipsburg, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/004,623

(22) Filed: Jan. 22, 2016

(65) Prior Publication Data

US 2016/0221895 A1    Aug. 4, 2016

Related U.S. Application Data

(63) Continuation of application No. 14/870,848, filed on Sep. 30, 2015, and a continuation-in-part of application No. 15/002,809, filed on Jan. 21, 2016.
(Continued)

(51) Int. Cl.
*C07C 6/12* (2006.01)
*C07C 4/18* (2006.01)
*B01J 29/80* (2006.01)
*B01J 35/10* (2006.01)
*B01J 29/22* (2006.01)
*B01J 29/24* (2006.01)
*B01J 29/44* (2006.01)
*B01J 29/46* (2006.01)
(Continued)

(52) U.S. Cl.
CPC ............ *B01J 29/80* (2013.01); *B01J 8/04* (2013.01); *B01J 29/22* (2013.01); *B01J 29/24* (2013.01); *B01J 29/44* (2013.01); *B01J 29/46* (2013.01); *B01J 29/67* (2013.01); *B01J 29/68* (2013.01); *B01J 29/74* (2013.01); *B01J 29/7446* (2013.01); *B01J 29/7453* (2013.01); *B01J 29/7461* (2013.01); *B01J 29/7476* (2013.01); *B01J 29/7484* (2013.01); *B01J 29/7492* (2013.01); *B01J 29/76* (2013.01); *B01J 29/7646* (2013.01); *B01J 29/7653* (2013.01); *B01J 29/7661* (2013.01); *B01J 29/7676* (2013.01); *B01J 29/7684* (2013.01); *B01J 29/7692* (2013.01); *B01J 35/002* (2013.01); *B01J 35/023* (2013.01); *B01J 35/108* (2013.01); *B01J 35/1014* (2013.01); *B01J 35/1019* (2013.01); *B01J 35/1023* (2013.01); *B01J 35/1033* (2013.01); *B01J 35/1052* (2013.01); *B01J 37/18* (2013.01); *C01B 39/265* (2013.01); *C07C 4/18* (2013.01); *C07C 6/126* (2013.01); *B01J 2208/027* (2013.01); *B01J 2229/186* (2013.01); *B01J 2229/42* (2013.01); *C07C 2521/04* (2013.01); *C07C 2529/18* (2013.01); *C07C 2529/22* (2013.01); *C07C 2529/24* (2013.01); *C07C 2529/40* (2013.01); *C07C 2529/44* (2013.01); *C07C 2529/46* (2013.01); *C07C 2529/80* (2013.01); *C07C 2529/87* (2013.01); *Y02P 20/52* (2015.11)

(58) Field of Classification Search
CPC .................................. C07C 6/12; C07C 4/18
USPC ................................ 585/475, 486, 488, 489
See application file for complete search history.

(56) References Cited

U.S. PATENT DOCUMENTS 3,354,078 A   11/1967   Miale et al.
3,506,731 A    4/1970   Frilette et al.
(Continued)

FOREIGN PATENT DOCUMENTS

CN    1296276    1/2005
CN    1666956    9/2005
(Continued)

OTHER PUBLICATIONS

Hincapie, Synthesis of mordenite nanocrystals, Microporous and Mesoporous Materials, (2004) pp. 19-26, 67, Science Direct, Elsevier Publishers.
(Continued)

*Primary Examiner* — Thuan D Dang
(74) *Attorney, Agent, or Firm* — Priya G. Prasad

(57) ABSTRACT

Disclosed is a catalyst composition and its use in a process for the conversion of a feedstock containing $C_8+$ aromatic hydrocarbons to produce light aromatic products, comprising benzene, toluene and xylene. The catalyst composition comprises a mordenite zeolite synthesized from TEA or MTEA, optionally at least one first metal of Group 10 of the IUPAC Periodic Table, and optionally at least one second metal of Group 11 to 15 of the IUPAC Periodic Table, wherein said mordenite zeolite has a mesopore surface area of greater than 30 m²/g and said mordenite zeolite comprises agglomerates composed of primary crystallites, wherein said primary crystallites have an average primary crystal size as measured by TEM of less than 80 nm and an aspect ratio of less than 2.

10 Claims, 7 Drawing Sheets

Related U.S. Application Data

(60) Provisional application No. 62/111,730, filed on Feb. 4, 2015.

(51) Int. Cl.

| | |
|---|---|
| *B01J 8/04* | (2006.01) |
| *B01J 37/18* | (2006.01) |
| *B01J 29/67* | (2006.01) |
| *B01J 29/68* | (2006.01) |
| *B01J 29/74* | (2006.01) |
| *B01J 29/76* | (2006.01) |
| *B01J 35/00* | (2006.01) |
| *B01J 35/02* | (2006.01) |
| *C01B 39/26* | (2006.01) |

(56) References Cited

U.S. PATENT DOCUMENTS

| | | |
|---|---|---|
| 3,527,825 A | 9/1970 | Pollitzer |
| 3,671,602 A | 6/1972 | Inoue et al. |
| 3,677,973 A | 7/1972 | Mitsche et al. |
| 3,679,575 A | 7/1972 | Bertolacini |
| 3,702,886 A | 11/1972 | Argauer et al. |
| 3,709,979 A | 1/1973 | Chu |
| 3,780,122 A | 12/1973 | Pollitzer |
| 3,832,449 A | 8/1974 | Rosinski et al. |
| 3,972,832 A | 8/1976 | Butter et al. |
| 4,016,218 A | 4/1977 | Haag et al. |
| 4,016,245 A | 4/1977 | Plank et al. |
| 4,039,479 A | 8/1977 | Gembicki et al. |
| 4,076,842 A | 2/1978 | Plank et al. |
| 4,083,886 A | 4/1978 | Michalko |
| 4,172,813 A | 10/1979 | Feinstein et al. |
| 4,291,186 A | 9/1981 | Tu |
| 4,300,012 A | 11/1981 | Tu et al. |
| 4,375,573 A | 3/1983 | Young |
| 4,439,409 A | 3/1984 | Puppe et al. |
| 4,536,486 A | 8/1985 | Lewis |
| 4,640,829 A | 2/1987 | Rubin |
| 4,698,217 A | 10/1987 | Valyocsik |
| 4,723,048 A | 2/1988 | Dufresne et al. |
| 4,826,667 A | 5/1989 | Zones et al. |
| 4,873,067 A | 10/1989 | Valyocsik et al. |
| 4,900,529 A | 2/1990 | Sanchez et al. |
| 4,954,325 A | 9/1990 | Rubin et al. |
| 5,077,254 A | 12/1991 | Travers et al. |
| 5,219,547 A | 6/1993 | Heilring et al. |
| 5,236,575 A | 8/1993 | Bennett et al. |
| 5,250,277 A | 10/1993 | Kresge et al. |
| 5,271,920 A | 12/1993 | Chang et al. |
| 5,336,478 A | 8/1994 | Dwyer et al. |
| 5,362,697 A | 11/1994 | Fung et al. |
| 5,658,839 A | 8/1997 | de Agudelo et al. |
| 5,763,720 A | 6/1998 | Buchanan et al. |
| 5,905,051 A | 5/1999 | Wu et al. |
| 5,929,296 A | 7/1999 | Merlen et al. |
| 5,942,651 A | 8/1999 | Beech, Jr. et al. |
| 6,060,417 A | 5/2000 | Kato et al. |
| 6,077,498 A | 6/2000 | Diaz Cabañas et al. |
| 6,150,292 A | 11/2000 | Merlen et al. |
| 6,359,184 B1 | 3/2002 | Kato et al. |
| 6,465,705 B1 | 10/2002 | Merlen et al. |
| 6,504,076 B1 | 1/2003 | Xiao et al. |
| 6,635,792 B2 | 10/2003 | Choi et al. |
| 6,756,030 B1 | 6/2004 | Rohde et al. |
| 6,815,570 B1 | 11/2004 | Negiz et al. |
| 6,846,964 B2 | 1/2005 | Xiao et al. |
| 6,867,340 B2 | 3/2005 | Oh et al. |
| 6,936,744 B1 | 8/2005 | Cheng et al. |
| 6,958,305 B2 | 10/2005 | Verduijn et al. |
| 6,972,348 B2 | 12/2005 | Negiz et al. |
| 6,984,764 B1 | 1/2006 | Roth et al. |
| 7,109,389 B2 | 9/2006 | Kong et al. |
| 7,148,391 B1 | 12/2006 | Buchanan et al. |
| 7,202,189 B2 | 4/2007 | Negiz et al. |
| 7,273,828 B1 | 9/2007 | Boldingh et al. |
| 7,297,831 B2 | 11/2007 | Lee et al. |
| 7,301,063 B2 | 11/2007 | Choi et al. |
| 7,304,195 B2 | 12/2007 | Choi et al. |
| 7,307,034 B2 | 12/2007 | Negiz et al. |
| 7,393,989 B2 | 7/2008 | Negiz et al. |
| 7,419,931 B2 | 9/2008 | Serra et al. |
| 7,456,124 B2 | 11/2008 | Boldingh et al. |
| 7,485,763 B2 | 2/2009 | Buchanan et al. |
| 7,553,791 B2 | 6/2009 | McMinn et al. |
| 7,566,810 B2 | 7/2009 | Boldingh et al. |
| 7,605,295 B1 | 10/2009 | Lafyatis et al. |
| 7,626,064 B1 | 12/2009 | Boldingh et al. |
| 7,629,499 B2 | 12/2009 | Serra Alfaro et al. |
| 7,663,010 B2 | 2/2010 | Levin |
| 7,687,423 B2 | 3/2010 | Moscoso et al. |
| 7,713,513 B2 | 5/2010 | Jan et al. |
| 7,897,825 B2 | 3/2011 | Levin |
| 8,030,239 B2 | 10/2011 | Oh et al. |
| 8,071,828 B2 | 12/2011 | Cao et al. |
| 8,163,966 B2 | 4/2012 | Levin |
| 8,183,424 B2 * | 5/2012 | Levin ............... B01J 29/064 585/323 |
| 8,202,506 B2 | 6/2012 | Lai et al. |
| 8,242,321 B2 | 8/2012 | Boldingh et al. |
| 8,242,322 B2 | 8/2012 | Boldingh |
| 8,481,443 B2 | 7/2013 | Levin et al. |
| 8,481,795 B2 | 7/2013 | Boldingh et al. |
| 8,933,283 B2 | 1/2015 | Kim et al. |
| 8,962,900 B2 | 2/2015 | Kim et al. |
| 8,962,901 B2 | 2/2015 | Kim et al. |
| 8,975,462 B2 | 3/2015 | Kim et al. |
| 9,006,125 B2 | 4/2015 | Levin et al. |
| 9,034,780 B2 | 5/2015 | Levin |
| 9,802,181 B2 | 10/2017 | Elia et al. |
| 2003/0036670 A1 | 2/2003 | Oh et al. |
| 2003/0125591 A1 | 7/2003 | Weber et al. |
| 2005/0250971 A1 | 11/2005 | Weber et al. |
| 2007/0185356 A1 | 8/2007 | Boldingh et al. |
| 2008/0035525 A1 | 2/2008 | Burgfels et al. |
| 2009/0112034 A1 * | 4/2009 | Levin ............... C07C 6/126 585/475 |
| 2010/0029467 A1 | 2/2010 | Inui et al. |
| 2012/0065446 A1 | 3/2012 | Boldingh |
| 2012/0244049 A1 | 9/2012 | Levin et al. |
| 2015/0298981 A1 | 10/2015 | Burton et al. |
| 2015/0353447 A1 | 12/2015 | Abichandani et al. |
| 2016/0220987 A1 | 8/2016 | Lai et al. |
| 2016/0221832 A1 | 8/2016 | Lai et al. |
| 2018/0029025 A1 | 2/2018 | Elia et al. |

FOREIGN PATENT DOCUMENTS

| | | |
|---|---|---|
| EP | 0 141 514 | 5/1985 |
| EP | 0 293 032 | 11/1988 |
| EP | 2 589 573 A | 5/2013 |
| KR | 1011733450000 | 8/2012 |
| WO | WO97/17290 | 5/1997 |
| WO | 00/06492 A | 2/2000 |
| WO | 2003/049857 | 6/2003 |
| WO | 2003049857 | 6/2003 |
| WO | 2008/147190 | 12/2008 |
| WO | 2008147190 | 12/2008 |
| WO | 2012/050748 | 4/2012 |
| WO | 2014/135662 A | 9/2014 |
| WO | WO2014/196791 | 12/2014 |

OTHER PUBLICATIONS

Margitfalvi, J.L. et al. "Zeolite supported Sn-Pt catalysts prepared by surface reactions," Journal of Molecular Catalysis A: Chemical 162 (2000), pp. 209-226, Elsevier Publishers.
U.S. Appl. No. 62/111,730, filed Feb. 4, 2015, Lai et al.
Baerlocher et al., *Atlas of Zeolite Framework Types*, Fifth Edition, 2001.
Burton et al, "On the estimation of average crystallite size of zeolites from the Scherrer equation: A critical evaluation of its application

(56) References Cited

OTHER PUBLICATIONS to zeolites with one-dimensional pore systems," Microporous and Mesoporous Materials, 117, pp. 75-90 (2009).
Lowell et al., *Characterization of Porous Solids and Powders: Surface Area, Pore Size and Density*, Springer Science (2004).
Miale et al. "*Catalysis by Crystalline Aluminosilcates IV. Attainable Catalytic Cracking Rate Constants, and Superactivity*," Journal of Catalysis, vol. 6, p. 278-287 (1966).
Olson et al., "*Chemical and Physical Properties of the ZSM-5 Substitutional Series*," Journal of Catalysis, vol. 61, p. 395-396 (1980).
Walter, D. "*Primary Particles—Agglomerates—Aggregates*," in Nanomaterials (ed. Deutsche Forschungsgemeinschaft (DFG), Wiley-VCH Verlag GmbH & Co. KGaA, Weinheim, Germany. Doi: 10.1002/9783527673919, pp. 1-24 (2013).
Weisz et al., "*Superactive Crystalline Aluminosilicate Hydrocarbon Catalysts*," Journal of Catalysis, vol. 4, p. 527-529 (1965).
IUPAC Periodic Table of the Elements, International Union of Pure and Applied Chemistry (May 2013).
Baerlocher et al., *Atlas of Zeolite Framework Types, Elsevier*, Sixth Revised Edition, 2007.
Halasz et al. "Indium and gallium containing ZSM-5 zeolites: acidity and catalytic activity in propane transformation," Catalysis Today 31, 1996, pp. 293-304.
Hincapie et al., "*Synthesis of mordenite nanocrystals*," Microporous and Mesoporous Materials, vol. 67, 2004, pp. 19-26.
Margitfalvi et al., "*Zeolite supported Sn-Pt catalysts prepared by surface reactions*," Journal of Molecular Catalysis A: Chemical, vol. 162, 2000, pp. 209-226.
Lu B., et al., "Direct synthesis of high-silica mordenite using seed crystals", Microporous and Mesoporous Materials, vol. 76, pp. 1-7, 2004.
Roberge, D., et al., "Dealurnination of zeolite beta by acid leaching: a new insight with two-dimensional multi-quantum and cross polarization 27AI MAS NMR", Physical Chemistry Chemical Physics, vol. 4, pp. 3128-3135, 2002.

* cited by examiner

SEM for Example 1

SEM for Example 2

SEM for Example 3

CATALYST COMPOSITIONS AND USE IN HEAVY AROMATICS CONVERSION PROCESSES

CROSS REFERENCE TO RELATED APPLICATIONS

This application claims the benefit of and priority to U.S. Ser. No. 62/111,730, filed 4 Feb. 2015, the disclosure of which is incorporated by reference in its entirety, and this application is a continuation of U.S. Ser. No. 14/870,848, filed 30 Sep. 2015, and this application is a continuation-in-part of U.S. Ser. No. 15/002,809, filed 21 Jan. 2016. This application is related to U.S. Ser. No. 15/714,204, co-filed herewith, and U.S. Ser. No. 62/111,737, filed 4 Feb. 2015.

FIELD

The invention relates to a catalyst composition useful for converting heavy aromatics, specifically $C_8+$ aromatics, to lighter aromatic products, particularly benzene, toluene and xylenes (hereinafter collectively referred to as BTX), to a process for producing the composition and to a process for using the composition in a heavy aromatics conversion process.

BACKGROUND

A source of benzene and xylenes is catalytic reformate, which is prepared by contacting a mixture of petroleum naphtha and hydrogen with a strong hydrogenation/dehydrogenation catalyst, such as platinum, on a moderately acidic support, such as a halogen-treated alumina. Usually, a $C_6$ to $C_8$ fraction is separated from the reformate and extracted with a solvent selective for aromatics or aliphatics to produce a mixture of aromatic compounds that is relatively free of aliphatics. This mixture of aromatic compounds usually contains BTX, along with ethylbenzene.

Refineries have also focused on the production of benzene and xylenes by transalkylation of lower value $C_9+$ aromatics with benzene or toluene to produce xylenes as increasingly important process. Chemical plants would ideally like to process as much of the heavy $C_9+$ aromatics as possible while minimizing and potentially removing the toluene/benzene co-feed. Both transalkylation activity and dealkylation activity are important for a successful catalyst system. Transalkylation is the ability to transalkylate methyl groups to form xylenes. Dealkylation activity is the ability to dealkylate ethyl and propyl groups present on the $C_9+$ aromatics to allow the formation of lower methyl/ring species that may transalkylate with higher methyl/ring species to form xylenes. Metal function is required to saturate olefins formed during dealkylation while maintaining the integrity of the aromatic saturations. As plants move to increased amounts of $C_9+$ in the feed, acceptable activity and catalyst life become challenging.

It has been shown that decoupling the dealkylation activity and transalkylation activity through use of a stacked bed system improves performance dramatically. One stacked bed catalyst system is disclosed in U.S. Pat. No. 5,942,651 and involves the steps of contacting a feed comprising $C_9+$ aromatic hydrocarbons and toluene under transalkylation reaction conditions with a first catalyst composition comprises a zeolite having a constraint index ranging from 0.5 to 3, such as ZSM-12, and a hydrogenation component. The effluent resulting from the first contacting step is then contacted with a second catalyst composition which comprises a zeolite having a constraint index ranging from 3 to 12, such as ZSM-5, and which may be in a separate bed or a separate reactor from the first catalyst composition to produce a transalkylation reaction product comprising benzene and xylene. The ethylbenzene in the feed and/or the ethylbenzene formed during transalkylation process are partially destroyed by dealkylation of ethylbenzene to benzene and ethylene.

Another stacked bed catalyst system is disclosed in U.S. Pat. No. 5,905,051 for a process for converting a hydrocarbon stream such as, for example, a $C_9+$ aromatic compound to $C_6$ to $C_8$ aromatic hydrocarbons, such as xylenes, by contacting the stream with a catalyst system comprising a first catalyst composition and a second catalyst composition, wherein said catalyst compositions are present in separate stages and are not physically mixed or blended and wherein said first catalyst composition is a metal-promoted, alumina- or silica-bound zeolite beta, and said second catalyst composition is ZSM-5 having incorporated therein an activity promoter selected from the group consisting of silicon, phosphorus, sulfur, and combinations thereof. According to the '051 patent, the use of the separate catalytic stages improves the conversion of $C_9+$ aromatic compounds and naphthalenes to xylenes and decreases the amount of undesirable ethylbenzene in the product. The ethylbenzene in the '051 product is about 3-7 wt. % of ethylbenzene based on the weight of $C_8$ aromatics fraction of the resulting product.

U.S. Pat. Nos. 8,183,424, 8,481,443, and 9,006,125 disclose improved performance with a stacked bed system in a process for producing xylene by transalkylation of a $C_9+$ aromatic hydrocarbon feedstock contacted with a $C_6$ and/or $C_7$ aromatic hydrocarbon and hydrogen with a first catalyst comprising (i) a first molecular sieve having a Constraint Index in the range of 3 to 12 and (ii) at least first and second different metals or compounds thereof of Groups 6 to 12 of the IUPAC Periodic Table of the Elements under conditions effective to dealkylate aromatic hydrocarbons and to saturate $C_2+$ olefins formed so as to produce a first effluent. At least a portion of the first effluent is then contacted with a second catalyst comprising a second molecular sieve having a Constraint Index less than 3 under conditions effective to transalkylate $C_9+$ aromatic hydrocarbons with said $C_6/C_7$ aromatic hydrocarbon to form a second effluent comprising xylene.

Stacked beds using at least one zeolite having MWW framework is disclosed in U.S. Pat. No. 8,163,966 in a process to produce a product containing xylenes comprising contacting a $C_9+$ aromatic feedstock, hydrogen, and a $C_6$-$C_7$ aromatic feedstock with a first catalyst comprising a first molecular sieve selected from the group consisting of MCM-22 and MCM-49 and 0.01 to 5 wt. % of a first metal element of Groups 6-10 under first conditions to form a first product, then contacting at least a portion of said first product with a second catalyst comprising a second molecular sieve selected from the group consisting of ZSM-12 and mordenite and 0 to 5 wt. % of a second metal element of Groups 6-10 and under second conditions to form a second product comprising xylenes.

Others have disclosed catalysts and processes for single bed systems. U.S. Pat. No. 6,867,340 discloses a catalyst for the disproportionation/transalkylation of various hydrocarbons that consists of a carrier and a metal component supported on the carrier. The carrier comprises 10 to 80 wt. % of mordenite and/or beta type zeolite with a mole ratio of silica/alumina ranging from 10 to 200; 0 to 70 wt. % of ZSM-5 type zeolite with a mole ratio of silica/alumina ranging from 30 to 500; and 5 to 90 wt. % of at least one inorganic binder selected from the group consisting of gamma-alumina, silica, silica alumina, bentonite, kaolin, clinoptilolite, and montmorillonite. The metal component comprises platinum and either tin or lead. The catalyst enables mixed xylenes to be produced at remarkably high yields from benzene, toluene and $C_9$ or higher aromatic compounds through disproportionation/transalkylation with a great reduction in aromatic loss. In addition, the catalyst can maintain its catalytic activity for a long period of time without deactivation.

U.S. Pat. No. 7,626,064 discloses a catalyst and a process for transalkylation of $C_7$, $C_9$, and $C_{10}$ aromatics to obtain a high yield of xylenes. The catalyst comprises a novel UZM-14 catalytic material comprising globular aggregates of crystallites having a MOR framework type with a mean crystallite length parallel to the direction of the 12-ring channels of about 60 nm or less and a mesopore volume of at least about 0.10 cc/gram. The UZM-14 catalyst is particularly active and stable in a transalkylation process.

U.S. Pat. No. 7,553,791 discloses a catalyst composition, a process for producing the composition and a process for the conversion of a feedstock containing $C_9$+ aromatic hydrocarbons to produce a resulting product containing lighter aromatic products and less than about 0.5 wt. % of ethylbenzene based on the weight of $C_8$ aromatics fraction of the resulting product. The $C_9$+ aromatic hydrocarbons are converted under the transalkylation reaction conditions to a reaction product containing xylene. The catalyst composition comprises (i) an acidity component having an alpha value of at least 300; and (ii) a hydrogenation component having hydrogenation activity of at least 300. The composition can be produced by incorporating at least one hydrogenation component into an acidity component having an alpha value of at least 300.

Even with these advances in transalkylation technology, there is a need for improved performance, particularly in a process for conversion of $C_{8+}$ aromatic hydrocarbons to lighter aromatic products.

SUMMARY

It has now been found that a single bed catalyst system comprising a high activity meso-mordenite zeolite exhibits improved $C_9$+ conversion and reduced aromatic ring loss as compared to other systems. Preferably, the catalyst composition is employed in the conversion of $C_{8+}$ aromatic hydrocarbons to lighter aromatic products.

The invention relates to a catalyst composition comprising a meso-mordenite zeolite (defined herein). The meso-mordenite zeolite is synthesized from tetraethylammonium cation (TEA) or methyltriethylammonium cation (MTEA). Optionally, the meso-mordenite zeolite has at least one first metal of Group 10 of the IUPAC Periodic Table. Preferably, 0.005 wt. % to 5.0 wt. % of said at least one first metal of Group 10 of the IUPAC Periodic Table, based on the weight of the catalyst composition. Optionally, the meso-mordenite zeolite has at least one second metal of Group 11 to 15 of the IUPAC Periodic Table. Preferably, 0.01 to 5.0 wt. % of said at least one second metal of Group 11 to 15 of the IUPAC Periodic Table, based on the weight of the catalyst composition. The meso-mordenite zeolite has a mesopore surface area of greater than 30 $m^2$/g and comprises agglomerates composed of primary crystallites. The primary crystallites have an average primary crystal size as measured by TEM of less than 80 nm and an aspect ratio of less than 2.

In addition, the invention relates to a process for the conversion of a feedstock comprising $C_{8+}$ aromatic hydrocarbons to lighter aromatic products. The process comprises the steps of contacting said feedstock and optionally hydrogen in the presence of any one of the catalyst compositions of this invention under suitable conversion conditions to produce said lighter aromatic products comprising benzene, toluene and xylene.

Typically, the $C_{8+}$ aromatic hydrocarbons in the feedstock comprise aromatic compounds having a boiling point in the range of about 135° C. to about 260° C., preferably a boiling point in the range of about 135° C. to about 230° C. at atmospheric pressure. Typically, the feedstock further comprises benzene or toluene or a mixture thereof.

DETAILED DESCRIPTION OF THE EMBODIMENTS

Definitions

Figure 1:
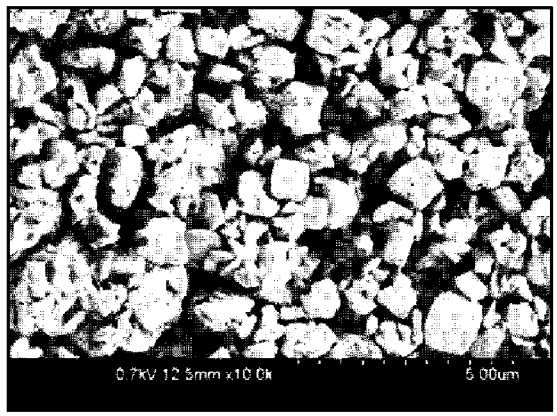
FIG. 1 shows a SEM of TEA-mordenite zeolite crystals of Comparative Example 1.

For the purpose of this specification and appended claims, the following terms are defined.

As used herein, the term "$C_n$ aromatic hydrocarbon" means an aromatic hydrocarbon having n carbon atom(s) per molecule, wherein n is a positive integer. The term "$C_{n+}$ aromatic hydrocarbon" means an aromatic hydrocarbon having at least n carbon atom(s) per molecule. The term "$C_{n-}$ aromatic hydrocarbon" means an aromatic hydrocarbon having no more than n carbon atom(s) per molecule.

As used herein, the term "aromatic" means substituted and unsubstituted mono- and poly-nuclear ring compounds. Compounds of the benzene series as well as compounds of an aromatic character which are or contain a heterocyclic ring are examples of aromatic compounds. These substituted aromatic compounds must, however, contain at least 1 hydrogen attached to the aromatic nucleus. The aromatic rings may be substituted with alkyl groups, aryl groups, alkaryl groups, hydroxy groups, amine groups, alkoxy groups, aryloxy groups, cycloalkyl groups, halide groups, and mixtures of these groups and other radicals which do not prevent the desired reaction.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, the term "lighter aromatic products" is defined to mean that the aromatic molecules in the products have fewer carbon atoms than the carbon atoms of the aromatic molecules in the feedstock. For example, paraxylene, one of the resulting products of $C_9+$ transalkylation with toluene and/or benzene, has 8 carbon atoms which are less than 9 or more carbon atoms in $C_9+$ aromatic molecules.

As used herein, the term "IUPAC Periodic Table" means the Periodic Table of the Elements of the International Union of Pure and Applied Chemistry, dated 1 May 2013, as it appears on the inside cover of The Merck Index, Twelfth Edition, Merck & Co., Inc., 1996.

As used herein, the term "meso-mordenite" means a mordenite zeolite synthesized from TEA or MTEA, having a mesopore surface area of greater than 30 $m^2/g$ and said mordenite zeolite comprising agglomerates composed of primary crystallites, wherein said primary crystallites have an average primary crystal size as measured by TEM of less than 80 nm and an aspect ratio of less than 2, as disclosed in U.S. Ser. No. 62/111,730, incorporated by reference herein. The mordenite zeolite of this invention and recited in the claims is referred to as meso-mordenite zeolite due to its high mesopore surface area.

As used herein, the term "TEA" means tetraethylammonium cation.

As used herein, the term "MTEA" means methyltriethylammonium cation.

As used herein, the term "molecular sieve" is used synonymously with the term "zeolite".

The term "aspect ratio" when used in reference to the primary crystals is defined as the longest dimension of the crystallite divided by the width of the crystallite, where the width of the crystallite is defined as the dimension of the crystallite in the middle of that longest dimension in a direction orthogonal to that longest dimension, as measured by TEM, is relatively low, for example, less than 2.0. Typically, the primary crystals are not elongated crystals having an aspect ratio greater than 2.0, or platelets.

As used herein, the term "primary crystal" denotes a single, indivisible crystal in contrast to an agglomerate. Primary crystals typically adhere together through weak physical interactions (rather than chemical bonds) to form agglomerates. The words "crystal" and "crystallite" are used herein interchangeably.

Catalyst Composition

The catalyst composition employed in the process of the invention comprises (i) a meso-mordenite zeolite synthesized from TEA or MTEA, optionally (ii) at least one first metal of Group 10 of the IUPAC Periodic Table, and optionally (iii) at least one second metal of Group 11 to 15 of the IUPAC Periodic Table, wherein said meso-mordenite zeolite has a mesopore surface area of greater than 30 $m^2/g$ and comprising agglomerates composed of primary crystallites, wherein said primary crystallites have an average primary crystal size as measured by TEM of less than 80 nm and an aspect ratio of less than 2.

The meso-mordenite zeolite has a very small crystal size and a high mesopore surface area, in particular by the selection of the synthesis mixture composition. The very small primary crystal size promotes access of reactant compounds to the active sites within the pores of the meso-mordenite, thereby increasing catalytic efficiency.

The meso-mordenite zeolite is synthesized from TEA or MTEA structure directing agents and has a mesopore surface area of greater than 30 $m^2/g$ and said meso-mordenite zeolite comprising agglomerates composed of primary crystallites, wherein said primary crystallites have an average primary crystal size as measured by TEM of less than 80 nm and an aspect ratio of less than 2. The mordenite zeolite of this invention is also referred to as meso-mordenite zeolite due to its high mesopore surface area.

The meso-mordenite zeolite comprises agglomerates, typically irregular agglomerates. The agglomerates are composed of primary crystallites which have an average primary crystal size as measured by TEM of less than 80 nm, preferably less than 70 nm and more preferably less than 60 nm, for example, less than 50 nm The primary crystallites may have an average primary crystal size as measured by TEM of, for example, greater than 20 nm, optionally greater than 30 nm Optionally, the primary crystals of the meso-mordenite zeolite have an average primary crystal size of less than 80 nm, preferably less than 70 nm, and in some cases less than 60 nm, in each of the a, b and c crystal vectors as measured by X-ray diffraction. The primary crystallites may optionally have an average primary crystal size of greater than 20 nm, optionally greater than 30 nm, in each of the a, b and c crystal vectors, as measured by X-ray diffraction.

The meso-mordenite zeolite will generally comprise a mixture of agglomerates of the primary crystals together with some unagglomerated primary crystals. The majority of the meso-mordenite zeolite, for example, greater than 80 weight % or greater than 90 weight % will be present as agglomerates of primary crystals. The agglomerates are typically of irregular form. For more information on agglomerates please see Walter, D. (2013) Primary Particles—Agglomerates—Aggregates, in Nanomaterials (ed. Deutsche Forschungsgemeinschaft (DFG)), Wiley-VCH Verlag GmbH & Co. KGaA, Weinheim, Germany doi: 10.1002/9783527673919, pages 1-24. Usefully, the meso-mordenite zeolite is not an aggregate.

Optionally, the meso-mordenite zeolite comprises at least 50% by weight, preferably at least 70% by weight, advantageously at least 80% by weight, more preferably at least 90% by weight and optionally substantially consists of said irregular agglomerates composed of primary crystallites having a primary crystal size of less than 80 nm, preferably less than 70 nm, and more preferably less than 60 nm, for example, less than 50 nm Preferably, the meso-mordenite zeolite of the invention comprises less than 10% by weight of primary crystallites having a size of more than 80 nm as assessed by TEM. Preferably, the meso-mordenite zeolite of the invention is composed of said irregular agglomerates composed of crystallites having a crystal size as measured by TEM of less than 80 nm Preferably, the meso-mordenite zeolite of the invention is substantially free, for example, contains less than 10% by number as assessed by TEM, of needle or platelet crystals.

Preferably, said primary crystallites of the meso-mordenite zeolite of the invention have an aspect ratio of less than 3.0, more preferably less than 2.0, wherein the aspect ratio is defined as the longest dimension of the crystallite divided by the width of the crystallite, where the width of the crystallite is defined as the dimension of the crystallite in the middle of that longest dimension in a direction orthogonal to that longest dimension, as measured by TEM.

Said agglomerates of said primary crystallites are typically of irregular form and may be referred to as being "secondary" particles because they are formed of agglomerates of the crystallites, which are the "primary" particles.

The primary crystallites may have a narrow particle size distribution such that at least 90% of the primary crystallites by number have a primary crystal size in the range of from 20 to 80 nm, preferably in the range of from 20 to 60 nm, as measured by TEM.

The meso-mordenite zeolite has a mesopore surface area as measured by BET of greater than 30 m²/g, preferably greater than 40 m²/g, and in some cases greater than 45 m²/g.

The meso-mordenite zeolite preferably has a total surface area of greater than 500 m²/g, more preferably greater than 550 m²/g, and in some cases greater than 600 m²/g. The total surface area includes the surface area of the internal pores (zeolite surface area) and also the surface area on the outside of the crystals (the external surface area). The total surface area is measured by BET.

Preferably, the ratio of the meso-mesopore surface area to the total surface area for the meso-mordenite zeolite is greater than 0.05.

The meso-mordenite zeolite preferably has a mesopore volume of greater than 0.1 mL/g, more preferably greater than 0.12 mL/g, and in some cases greater than 0.15 mL/g The ratio $Si:Al_2$ of the meso-mordenite zeolite of the invention is preferably greater than 10 and may be in the range of, for example, from 10 to 60, preferably from 15 to 40. The ratio $Si:Al_2$ of the post-treated meso-mordenite zeolite is preferably in the range of from 40 to 300, more preferably from 60 to 150.

The meso-mordenite zeolite may be prepared by the method comprising the steps of:
a) providing a synthesis mixture comprising a silicon source, an aluminum source, an alkali metal (M) hydroxide, a source of a structure directing agent (SDA) selected from the group consisting of tetraethylammonium cation (TEA), methyltriethylammonium cation (MTEA) and mixtures thereof, optional seed crystals and water, said synthesis mixture having a composition including the following molar ratios:

|  |  |
| --- | --- |
| $Si:Al_2$ | 15-40 |
| $OH^-:Si$ | ≤0.32 |
| $M^+:Si$ | ≤0.32 |
| SDA:Si | ≤0.10 |
| $H_2O:Si$ | <20 | b) subjecting said synthesis mixture to crystallization conditions to form crystals of a meso-mordenite zeolite comprising the structure directing agent (SDA) within its pores. The components of the synthesis mixture are combined and maintained under crystallization conditions.

Suitable sources of silicon (Si) include silica, colloidal suspensions of silica, precipitated silica, alkali metal silicates such as potassium silicate and sodium silicate, tetraalkyl orthosilicates, and fumed silicas such as Aerosil and Cabosil. Preferably, the source of Si is a precipitated silica such as Ultrasil (available from Evonik Degussa) or HiSil (available from PPG Industries).

Suitable sources of aluminum (Al) include aluminum sulfate, aluminum nitrate, aluminum hydroxide, hydrated alumina such as boehmite, gibbsite and/or pseudoboehmite, sodium aluminate and mixtures thereof. Other aluminum sources include, but are not limited to, water-soluble aluminum salts, or an aluminum alkoxide, such as aluminum isopropyloxide, or an aluminum metal, such as aluminum in the form of chips. Preferably, the aluminum source is sodium aluminate, for example an aqueous solution of sodium aluminate with a concentration in the range of 40 to 45%, or aluminum sulfate, for example an aluminum sulfate solution with a concentration in the range of from 45 to 50%.

Alternatively or in addition to previously mentioned sources of Si and Al, aluminosilicates may also be used as a source of both Si and Al.

Preferably, the $Si:Al_2$ ratio in the synthesis mixture is in the range of from 15 to 40, more preferably from 20 to 30.

The synthesis mixture also contains a source of alkali metal cation $M^+$. The alkali metal cation $M^+$ is preferably selected from the group consisting of sodium, potassium and mixtures of sodium and potassium cations. Sodium cation is preferred. Suitable sodium sources may be, for example, a sodium salt such as NaCl, NaBr or $NaNO_3$, sodium hydroxide or sodium aluminate, preferably sodium hydroxide or sodium aluminate. Suitable potassium sources may be, for example, potassium hydroxide or potassium halide such as KCl or KBr, or potassium nitrate. Preferably, the ratio $M^+$:Si in the synthesis mixture is in the range of from 0.15 to 0.32, more preferably from 0.20 to 0.32. Optionally, the ratio $M^+$:Si is less than 0.30.

The synthesis mixture also contains a source of hydroxide ions, for example, an alkali metal hydroxide such as sodium hydroxide or potassium hydroxide. Hydroxide can also be present as a counter ion of the structure directing agent or by the use of aluminum hydroxide as a source of Al. Preferably the range $OH^-$:Si is greater than 0.13, and may, for example, be in the range of from 0.15 to 0.32, preferably from 0.20 to 0.32. Optionally, the $OH^-$:Si ratio is less than 0.30.

The synthesis mixture optionally comprises seeds. The seeds may be any suitable zeolite seed crystals, such as, for example, ZSM-5 seed crystals or ZSM-11 seed crystals or mordenite seed crystals. Preferably, the seeds are meso-mordenite crystals. The seeds may, for example, be present in an amount from 0 wt. % to 10 wt. %, preferably from 0.01 wt. % to 10 wt. % such as from 0.1 wt. % to 5.0 wt. % of the synthesis mixture. In a preferred embodiment, the synthesis mixture comprises seeds.

The structure directing agent, also referred to as SDA, is TEA and/or MTEA, preferably TEA, and may be present in any suitable form, for example as a halide, but is preferably present in its hydroxide form. Suitable sources of the structure directing agent include TEABr, TEAOH, MTEACl, MTEABr and MTEAOH. A preferred source of structure directing agent is TEABr. Preferably, the ratio SDA:Si is in the range of from 0.005 to 0.10, more preferably from 0.02 to 0.10, especially from 0.02 to 0.05.

The synthesis of small crystal meso-mordenite is favored by having a relatively high solids content in the synthesis mixture. Preferably, the $H_2O$:Si ratio is no more than 20, for example, in the range of from 5 to 20, preferably from 5 to 17, especially from 10 to 17. The synthesis mixture may, for example, have a composition, expressed in terms of mole ratios, as indicated in the following Table 1.

TABLE 1

| Mole ratio | Preferred | More preferred | Especially preferred |
| --- | --- | --- | --- |
| $Si:Al_2$ | 15 to 40 | 20 to 35 | 20 to 30 |
| $OH^-:Si$ | 0.15 to 0.32 | 0.20 to 0.32 | 0.20 to <0.30 |
| $M^+:Si$ | 0.15 to 0.32 | 0.20 to 0.32 | 0.20 to <0.30 |
| SDA:Si | 0.005 to 0.10 | 0.02 to 0.10 | 0.02 to 0.05 |
| $H_2O:Si$ | 5 to 20 | 5 to 17 | 10 to 17 |

Crystallization can be carried out under either static or stirred conditions in a suitable reactor vessel, such as for example, polypropylene jars or Teflon® lined or stainless steel autoclaves. Suitable crystallization conditions include a temperature of about 100° C. to about 200° C., such as about 135° C. to about 160° C. Preferably, the temperature is less than 145° C. The synthesis mixture may be held at the elevated temperature for a time sufficient for crystallization to occur at the temperature used, for example, from about 1 day to about 100 days, optionally from 1 to 50 days for example about 2 days to about 40 days. The synthesis mixture may in some cases be maintained at a first temperature for a first period of from 1 hour to 10 days and then raised to a second, higher temperature for a period of from 1 hour to 40 days. After the crystallization step, the synthesized crystals are separated from the liquid and recovered.

In its as-synthesized form, the meso-mordenite zeolite typically has a chemical composition having the following molar relationship:

$$mQ:nSiO_2:Al_2O_3$$

wherein
0.001≤m/n≤0.1, for example 0.001≤m/n≤0.05,
n is at least 10, for instance from 10 to 60, preferably from 15 to 40, and
Q is the structure directing agent.

Since the as-synthesized meso-mordenite zeolite contains the structure directing agent within its pore structure, the product is usually activated before use in such a manner that the organic part of the structure directing agent, i.e., TEA and/or MTEA, is at least partially removed from the zeolite.

The calcined meso-mordenite zeolite is optionally prepared by calcining the mordenite zeolite to remove the structure directing agent. The meso-mordenite zeolite may also be subjected to an ion-exchange step to replace the alkali or alkaline earth metal ions present in the as-synthesized product with other cations. Preferred replacing cations include metal ions, hydrogen ions, hydrogen precursor such as ammonium ions and mixtures thereof, more preferably hydrogen ions or hydrogen precursors. For instance, the meso-mordenite zeolite may be subjected to an ion-exchange step to replace the alkali or alkaline earth metal ions with ammonium cations, followed by calcination to convert the meso-mordenite zeolite in ammonium form to a meso-mordenite zeolite in hydrogen form. In one embodiment, the meso-mordenite zeolite is first subjected to a calcination step, sometimes referred to as a "pre-calcination" to remove the structure directing agent from the pores of the meso-mordenite zeolite, followed by an ion-exchange treatment, followed by a further calcination step. However, it has been found that for the meso-mordenite zeolite of the present invention, a pre-calcination step is not always required. In an alternative embodiment, the meso-mordenite zeolite is thus subjected to an ion-exchange treatment without being subjected to a prior calcination step (or pre-calcination), and, following the ion exchange treatment, is calcined to remove the structure directing agent from the pores, thereby providing the calcined meso-mordenite zeolite used in this invention.

The ion-exchange step may involve, for example, contacting the meso-mordenite zeolite with an aqueous ion exchange solution. Such contact may be take place, for example, from 1 to 5 times. The contacting with the ion exchange solution is optionally at ambient temperature, or alternatively may be at an elevated temperature. For example, the meso-mordenite zeolite may be ion exchanged by contact with aqueous ammonium nitrate solution at room temperature followed by drying and calcination.

Suitable calcination conditions include heating at a temperature of at least about 300° C., preferably at least about 370° C. for at least 1 minute and generally not longer than 20 hours, for example, for a period of from 1 hour to 12 hours. While subatmospheric pressure can be employed for the thermal treatment, atmospheric pressure is desired for reasons of convenience. The thermal treatment can be performed at a temperature up to about 925° C. For instance, the thermal treatment can be conducted at a temperature of from 400° C. to 600° C., for instance from 500° C. to 550° C., in the presence of an oxygen-containing gas.

The calcined meso-mordenite zeolite typically has a chemical composition having the following molar relationship:

$$nSiO_2:Al_2O_3$$

wherein n is at least 10, for example 10 to 60, more particularly 15 to 40.

The catalyst composition of this invention comprises a meso-mordenite zeolite, optionally at least one first metal of Group 10 of the IUPAC Periodic Table, and optionally at least one second metal of Group 11 to 15 of the IUPAC Periodic Table. Typically, meso-mordenite zeolite is present in an amount from about 1 to about 99 wt. %, such as from about 20 up to about 80 wt. % based on the total weight of the catalyst composition.

In addition to the meso-mordenite zeolite, the catalyst comprises optionally at least one first metal of Group 10 of the IUPAC Periodic Table, and optionally at least one second metal of Group 11 to Group 15 of the IUPAC Periodic Table. The first metal of Group 10 metal includes, but is not limited to, one or more of nickel (Ni), palladium (Pd), platinum (Pt), and compounds containing netural metals or ions thereof, preferably platinum or palladium. The second metal of Group 11 to Group 15 includes, but is not limited to, one or more of copper (Cu), silver (Ag), gold (Au), zinc (Zn), cadmium (Cd), gallium (Ga), indium (In), tin (Sn), bismuth (Bi), and compounds containing netural metals or ions thereof, preferably copper, gallium or tin.

The catalyst composition comprises from at least about 0.005 wt. %, or 0.01 wt. %, or 0.05 wt. %, or 0.10 wt. % up to about 1.0 wt. %, 2.0 wt. %, 3.0 wt. %, or 4.0 wt. %, or 5.0 wt. %, of the first metal of Group 10 of the IUPAC Periodic Table, based on the weight of the catalyst composition. The catalyst composition may comprise from about 0.01 wt. % of the metal, such as greater than or equal to 0.02 wt. % up to 0.5 wt. %, 1.0 wt. %, 2.0 wt. %, or 3.0 wt. %, or 4.0 wt. %, or 5.0 wt. % of such first metal. In one or more embodiments of the invention, the catalyst composition has at least one first metal of Group 10 in the range of about 0.005 wt. % to about 5.0 wt. %, based on the weight of the catalyst composition.

The catalyst composition comprises from at least about 0.005 wt. %, or 0.01 wt. %, or 0.05 wt. %, or 0.10 wt. % up to about 0.50 wt. %, 0.75 wt. %, 1.0 wt. %, or 1.25 wt. %, or 1.5 wt. %, or 2.0 wt. % of the second metal of Group 11 to Group 15 of the IUPAC Periodic Table, based on the weight of the catalyst composition. The catalyst composition may comprise from about 0.005 wt. % of the metal, such as greater than or equal to 0.01 wt. % up to 0.5 wt. %, 0.75 wt. %, 1.0 wt. %, or 1.25 wt. %, or 1.5 wt. %, or 2.0 wt. % of such second metal, based on the weight of the catalyst composition. In one or more alternatives of the invention, the catalyst composition has at least one second metal of Group 11 to Group 15 in the range of about 0.01 to about 1.5 wt. %, based on the weight of the catalyst composition.

Those skilled in the art will appreciate that the first metal comprises one or more metals of greater catalytic hydrogenation activity, for example, Pt, and/or Pd, a lesser amount of the first metal may be needed, for example, in the range of about 0.005 wt. % to about 0.1 wt. %, based on the weight of the catalyst composition, such as for example, in the range of about 0.01 wt. % to about 0.6 wt. %, or about 0.01 wt. % to about 0.05 wt. %, based on the weight of the catalyst composition.

When the metal component comprises one or more metals of lesser hydrogenation activity, for example, one or more of Ga, In, Zn, Cu, and Sn, a greater amount of the second metal may be needed, for example, in the range of about 0.005 wt. % to about 5 wt. %, based on the weight of the catalyst composition, such as about 0.01 wt. % to about 1.5 wt. %, or about 0.1 wt. % to about 1 wt. %, based on the weight of the catalyst composition. When the catalyst composition comprises two metals, for example, the two metals may be present either as distinct metals, or as an alloy of the two metals. When two metals form an alloy, the alloy may have hydrogenation activity different to the hydrogenation activity of either of the individual metals.

The metal component, for example, the first metal and/or the second metal, may be provided on the catalyst composition in any manner, for example, by conventional methods such as impregnation or ion exchange of the meso-mordenite zeolite with a solution of a compound of the relevant metal before or after forming the catalyst particle.

It may be desirable to incorporate another material into the meso-mordenite zeolite in the catalyst composition that is resistant to the temperatures and other conditions employed in the process of the invention. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides.

The catalyst of this invention further comprising at least one binder selected from the group consisting of alumina, silica, clay, titania, zirconia and a mixture of two or more thereof. Use of a material in conjunction with the meso-mordenite, i.e. combined therewith or present during its synthesis, which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may be incorporated into, for example, naturally occurring clays, for example bentonite and kaolin, to improve the crush strength of the catalyst composition under commercial operating conditions. It is desirable to provide a catalyst composition having good crush strength because in commercial use, it is desirable to prevent the catalyst composition from breaking down into powder-like materials.

Naturally occurring clays that can be composited with the meso-mordenite zeolite as a binder for the catalyst composition include the montmorillonite and kaolin family, which families include the subbentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the meso-mordenite zeolite may be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form to facilitate extrusion of the catalyst composition.

Each zeolite is usually admixed with the binder or matrix material so that the final catalyst composition contains the binder or matrix material in an amount ranging from 5 to 90 wt. %, and typically from 10 to 60 wt. %, based on the weight of the catalyst composition.

Prior to use, steam treatment of the catalyst composition may be employed to minimize the aromatic hydrogenation activity of the catalyst composition. In the steaming process, the catalyst composition is usually contacted with from 5% to 100% steam, at a temperature of at least 260° C. to 650° C. for at least one hour, specifically 1 to 20 hours, at a pressure of 100 to 2590 kPA-a and a WHSV of about 0.002 $hr^{-1}$ to about 20 $hr^{-1}$.

In addition, prior to contacting the catalyst composition with the hydrocarbon feed, the hydrogenation component can be sulfided. This is conveniently accomplished by contacting the catalyst with a source of sulfur, such as hydrogen sulfide, at a temperature ranging from about 320° C. to 480° C. The source of sulfur can be contacted with the catalyst via a carrier gas, such as hydrogen or nitrogen.

After contacting the catalyst composition with the hydrocarbon feed, the catalyst may be deactivated due to coking or metal agglomerization. The deactivated catalyst can be regenerated conveniently by coke burning with a stream comprising oxygen or oxygen containing compounds, such as, ozone, oxochlorine, carbon dioxide or the like, metal re-dispersing using oxdization-reduction cycle, oxochloride treatment or the like, washing with liquid hydrocarbons or aqueous solution of inorganic and/or organic chemical compounds, such as, water, ethanol, acetone, or the like, or rejuvenation with a stream comprising hydrogen. Regeneration or rejuvenation can be performed at a temperature range from ambient to about 600° C., a pressure range of about 100 kPa-a to about 5000 kPa-a, and WHSV of about 0.2 $hr^{-1}$ to about 100 $hr^{-1}$.

Feedstock

The feedstock used in the process of the invention comprises one or more aromatic compounds containing at least 8 carbon atoms, for example, $C_{8+}$ aromatic hydrocarbons. Specific comprising $C_{8+}$ aromatic hydrocarbons include ethylbenzene and dimethylbenzene isomers. Typically, such $C_{8+}$ aromatic hydrocarbons comprise aromatic compounds having a boiling point in the range of about 135 to about 230° C. at atmospheric pressure.

In one or more embodiments, such feedstock comprises aromatic compounds having 9 or more carbon atoms, for example, $C_{9+}$ aromatic hydrocarbons. Specific $C_9+$ aromatic compounds found in a typical feed include mesitylene (1,3,5-trimethylbenzene), durene (1,2,4,5-tetramethylbenzene), hemimellitene (1,2,3-trimethylbenzene), pseudocumene (1,2,4-trimethylbenzene), ethyltoluene, ethylxylene, 1,2-methylethylbenzene, 1,3-methylethylbenzene, 1,4-methylethylbenzene, propyl-substituted benzenes, butyl-substituted benzenes, dimethylethylbenzenes, methylpropylbenzene, methylbutylbenzene, and a mixture of two or more thereof.

Suitable sources of the $C_9+$ aromatics are any $C_9+$ fractions from any refinery process that is rich in aromatics. This aromatics fraction contains a substantial proportion of $C_9+$ aromatics, for example, at least 80 wt. % $C_9+$ aromatics, wherein preferably at least 80 wt. %, and more preferably more than 90 wt. %, of the hydrocarbons will range from $C_9$ to $C_{12}$. Typical refinery fractions which may be useful include catalytic reformate, fluidized catalytic cracking (FCC) naphtha or thermoform catalytic cracking (TCC) naphtha.

The feedstock may also comprise benzene or toluene or a mixture of benzene and toluene. Thus, in one practical embodiment, the feed to the reactor for transalkylation comprises ethylbenzene, $C_9+$ aromatics hydrocarbons and toluene. The feedstock may also include recycled/unreacted/produced benzene, toluene, ethylbenzene, and $C_9+$ aromatics that is obtained by distillation of the effluent product of the transalkylation reaction itself. Typically, toluene constitutes from about 5 wt. % to about 90 wt. % and $C_9+$ constitutes from about 10 to about 95 wt. % of the feedstock. In a typical light feedstock, toluene constitutes from about 40 wt. % to about 90 wt. %, such as from 50 wt. % to 70 wt. % of the entire feed, whereas the $C_9+$ aromatics component constitutes from 10 to 60 wt. %, such as from 30 to 50 wt. %, of the entire feedstock to the reactor. In a typical heavy feed, toluene constitutes from about 15 wt. % to about 50 wt. %, such as from 25 to 40 wt. % of the entire feed, whereas the $C_9+$ aromatics component constitutes from 50 to 85 wt. %, such as from 60 to 75 wt. %, of the entire feed to the reactor.

Hydrocarbon Conversion Process

The process for the conversion of a feedstock comprising $C_{8+}$ aromatic hydrocarbons to lighter aromatic products comprises the steps of contacting said feedstock and optionally hydrogen in the presence of any one of the catalyst compositions of this invention under suitable conversion conditions to produce said lighter aromatic products comprising benzene, toluene and xylene.

The process can be conducted in any appropriate reactor including a radial flow, fixed bed, continuous flow or fluid bed reactor. In one alternative, the reactor for contacting said feedstock under said suitable conversion conditions comprises at least one single fixed catalyst bed of said catalyst. In another alternative, the reactor for contacting said feedstock under said suitable conversion comprises at least one moving catalyst bed of said catalyst.

The conversion conditions typically include a temperature ranging from about 340° C. to about 515° C., such as from about 400° C. to about 454° C.; a pressure from about 380 to kPa-a about 4240 kPa-a, such as from about 1480 kPa-a to about 3550 kPa-a; a hydrogen to hydrocarbon molar ratio from about 1 to about 5, such as from about 1 to about 3 and a WHSV of about 0.2 $hr^{-1}$ to about 100 $hr^{-1}$, such as from 1 $hr^{-1}$ to about 100 $hr^{-1}$. The conversion conditions are sufficient to convert the heavy aromatic feed to a product containing substantial quantities of $C_6$-$C_8$ aromatic compounds, such as benzene, toluene and xylenes, especially benzene and xylene. The conversion conditions also are sufficient to convert the ethylbenzene in the feed to benzene and ethane.

EXAMPLES

The following examples illustrate the present invention. Numerous modifications and variations are possible and it is to be understood that within the scope of the appended claims, the invention may be practiced otherwise than as specifically described herein.

Experimental

Measurement of Average Primary Particle Size and Primary Particle Size Distribution The measurement of average primary particle size and primary particle size distribution was carried out as follows. Several TEM photographs of the zeolite sample were taken; primary particles were identified and measured. For each primary particle having an aspect ratio greater than 1, the longest dimension was identified by drawing a line between the two points at the edge of the particle which were the furthest apart. Then the length of the primary particle along a 45° diagonal to that longest dimension and passing through the mid-point of that longest dimension was measured as the particle size. Each measurement was grouped by being assigned to one of about 10 particle size ranges covering the range of sizes found in the sample. More than 300 primary particles were measured and then the numbers in each particle size range were plotted to show the particle size distribution, as shown in FIG. 10. For example, size ranges centered around 187.5, 250, 312.5, 375, 437.5, 500, 562.5 and 625 Angstroms could be used. The percent (%) crystals value on the y-axis was calculated from: Number of particles in each group/total number of particles measured multiplied by 100. The average particle size was calculated as the arithmetical mean based on the grouped results.

Measurement of Total Surface Area and Mesopore Surface Area by BET

The total BET and the t-Plot micropore surface area were measured by nitrogen adsorption/desorption with a Micromeritics Tristar II 3020 instrument after degassing of the calcined zeolite powders for 4 hrs. at 350° C. The mesopore surface area was obtained by the subtraction of the t-plot micropore from the total BET surface area. The mesopore volume was derived from the same data set. More information regarding the method can be found, for example, in "Characterization of Porous Solids and Powders: Surface Area, Pore Size and Density", S. Lowell et al., Springer, 2004.

X-Ray Diffraction Patterns

The X-ray diffraction data (powder XRD or XRD) were collected with a Bruker D4 Endeavor diffraction system with a VANTEC multichannel detector using copper K-alpha radiation. The diffraction data were recorded by scanning mode with 0.018 degrees two-theta, where theta is the Bragg angle, and using an effective counting time of about 30 seconds for each step.

Measurement of the Crystal Sizes in the a, b and c Vectors

The crystal sizes in the a, b and c crystal vectors were calculated based on the three (200), (020) and (002) peaks in the X-ray diffraction patterns using the Scherrer equation (P. Scherrer, N.G.W. Gottingen, Math-Pys., 2, p. 96-100 (1918)). The method and its application to zeolites are also described in A. W. Burton, K. Ong, T. Rea, I. Y. Chan, Microporous and Mesoporous Materials, 117, p. 75-90 (2009). For the measurements described herein the Jade version 9.5.1 X-ray diffraction analysis software by Materials Data, Inc., was used to perform the calculation.

Alpha Value

The alpha value is a measure of the cracking activity of a catalyst and is described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test used herein included a constant temperature of 538° C. and a variable flow rate as described in detail in the Journal of Catalysis, Vol. 61, p. 395 (1980).

Example 1

TEA-Mordenite Crystals (Comparative)

TEA-Mordenite crystals were synthesized from a mixture prepared from water, a 47% Aluminum sulfate solution, a 50% TEABr solution, Ultrasil™ PM Modified silica (obtainable from Evonik Ind. AG), and a 50% sodium hydroxide solution. The mixture had the following molar composition:

| | |
|---|---|
| $SiO_2/Al_2O_3$ | ~40 |
| $H_2O/SiO_2$ | ~9.33 |
| $OH^-/SiO_2$ | ~0.22 |
| $Na^+/SiO_2$ | ~0.37 |
| $TEA/SiO_2$ | ~0.31 |

The mixture was reacted at 300° F. (150° C.) in a autoclave for 48 hours. The product was filtered, washed with deionized (DI) water and dried at 250° F. (121° C.). The X-ray diffraction (XRD) pattern of the as-synthesized material showed the typical pure phase of mordenite topology. The scanning electron microscope image (SEM), FIG. 1, of the as-synthesized material showed that the material was composed of large micron-sized, 0.2 μm to 1.0 crystals.

The as-synthesized mordenite crystals were converted into the hydrogen form by three ion exchanges with ammonium nitrate solution at room temperature, followed by drying at 250° F. (121° C.) and calcination at 1000° F. (538° C.) for 6 hours. The resulting H-form, mordenite crystals had a total surface area (SA), i.e., a micro pore SA+mesopore SA, of 625/(616+9) m²/g, and a mesopore volume of 0.0574 cc/g. The $SiO_2/Al_2O_3$ molar ratio was 33.4, and the Alpha Value was 610.

Example 2

Meso-Mordenite Crystals (NaOH/Si of 0.29 Molar)

Meso-mordenite crystals were synthesized from a mixture prepared from 10,300 g of water, 670 g of TEABr (50% solution), 2,120 g of Ultrasil™ PM Modified silica, 487 g of sodium aluminate solution (45%), and 510 g of 50% sodium hydroxide solution. After preparing this mixture, 20 g of mordenite seeds was then added to the mixture. The mixture had the following molar composition:

| | |
|---|---|
| $SiO_2/Al_2O_3$ | ~26.08 |
| $H_2O/SiO_2$ | ~19.48 |
| $OH^-/SiO_2$ | ~0.29 |
| $Na^+/SiO_2$ | ~0.29 |
| $TEA/SiO_2$ | ~0.05 |

Figure 2:
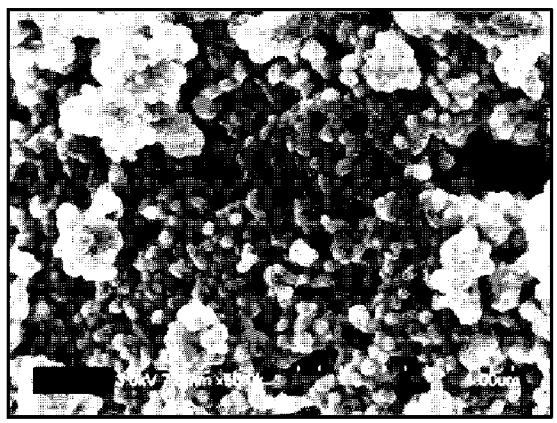
FIG. 2 shows a SEM of the meso-mordenite zeolite crystals of Example 2.

The mixture was reacted at 300° F. (150° C.) in a 5-gal autoclave with stirring at 250 RPM for 72 hours. The product was filtered, washed with deionized (DI) water and dried at 250° F. (121° C.). The XRD pattern of the as-synthesized material showed the typical pure phase of Mordenite topology. The SEM, FIG. 2, of the as-synthesized material showed a morphology of irregularly-shaped aggregates composed of small crystallites of ≤0.05 μm. More uniform crystal size and morphology were produced from 5-gal reaction. The as-synthesized crystals were converted into the hydrogen form by three ion exchanges with ammonium nitrate solution at room temperature, followed by drying at 250° F. (121° C.) and calcination at 1000° F. (538° C.) for 6 hours. The resulting meso-mordenite crystals had a $SiO_2/Al_2O_3$ molar ratio of ~21, total (micro+meso) surface area of 624 (579+44) m²/g and meso-pore volume of 0.243 cc/g. The hexane sorption was 61.8 mg/g, and the Alpha Value was 780. Based on the outcome of this example, it was concluded that small meso-mordenite crystals with high mesopore volume and surface area could be synthesized from reaction mixtures with NaOH/Si of <0.30 molar.

Example 3

Meso-Mordenite Crystals (NaOH/Si of 0.29 Molar)

Meso-mordenite crystals were synthesized from a mixture prepared from 9,300 g of water, 804 g of tetraethylammonium bromide (TEABr) (50% solution), 2,544 g of Ultrasil™ PM Modified silica, 584 g of sodium aluminate solution (45%), and 612 g of 50% sodium hydroxide solution. Then, 30 g of mordenite seeds was added to the mixture. The mixture had the following molar composition:

| | |
|---|---|
| $SiO_2/Al_2O_3$ | ~26.1 |
| $H_2O/SiO_2$ | ~15.11 |
| $OH^-/SiO_2$ | ~0.29 |
| $Na^+/SiO_2$ | ~0.29 |
| $TEA/SiO_2$ | ~0.05 |

Figure 3:
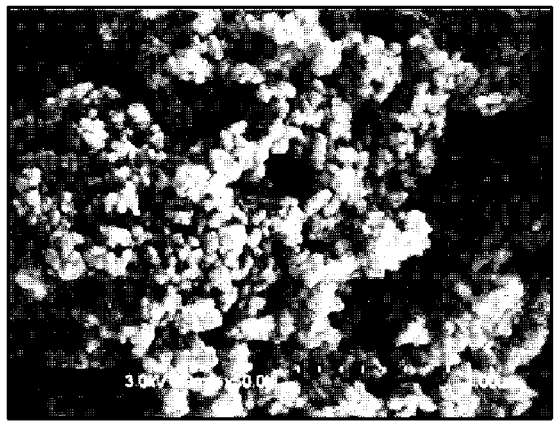
FIG. 3 shows a SEM of the meso-mordenite zeolite crystals of Example 3.

The mixture was reacted at 290° F. (143.3° C.) in a 5-gal autoclave with stirring at 250 RPM for 72 hours. The product was filtered, washed with deionized (DI) water and dried at 250° F. (121° C.). The XRD pattern of the as-synthesized material showed the typical pure phase of mordenite topology. The SEM, FIG. 3, of the as-synthesized material showed morphology of irregularly-shaped agglomerates composed of small crystallites of ≤0.05 μm. Smaller and more uniform crystals were produced from this improved synthesis as compared to prior art lower porosity mordenite crystals. The resulting as-synthesized meso-mordenite crystals showed a $SiO_2/Al_2O_3$ molar ratio of about 20.7.

The as-synthesized crystals meso-mordenite were converted into the hydrogen form by three ion exchanges with ammonium nitrate solution at room temperature, followed by drying at 250° F. (121° C.) and calcination at 1000° F. (538° C.) for 6 hours. The resulting H-form, meso-mordenite crystals had a total (micro+meso) surface area of 637(580+56) m²/g and meso-pore volume of 0.43 cc/g. The hexane sorption was 53.3 mg/g and the Alpha Value was 1,200.

Example 4

65/35 TEA-Mordenite/Alumina Catalyst (Comparative)

A catalyst was made from a mixture of 65 parts (basis: calcined 538° C.) of the TEA-mordenite crystal from Example 1 and 35 parts of pseudoboehmite alumina of Versal™ 300 (obtainable from UOP LLC; basis: calcined 538° C.) in a muller. Sufficient water was added to produce an extrudable paste on an extruder. The mixture of TEA-mordenite, pseudoboehmite alumina, and water was extruded into an extrudate, and then dried at 121° C. The dried extrudate was calcined in nitrogen ($N_2$) at 538° C. to decompose and remove the organic template. The $N_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 116° C. and calcined in air at 534° C. After air calcination, properties of the resulting catalyst were: Alpha Value=640; hexane sorption: 62 mg/g; BET surface area, total(micro+meso) of 468/(296+172) m$^2$/g.

Example 5

65/35 Meso-Mordenite/Alumina Catalyst

A catalyst was made from a mixture of 65 parts (basis: calcined 538° C.) of small meso-mordenite crystal from Example 2 and 35 parts of pseudoboehmite alumina of Versal™ 300; basis: calcined 538° C.) in a muller. Sufficient water was added to produce an extrudable paste on an extruder. The mixture of meso-mordenite, pseudoboehmite alumina, and water was extruded into an extrudate, and then dried at 121° C. The crush strength of the resulting extrudates was measured and showed to be 108 lbs/in (19 kg/cm). The dried extrudate was calcined in nitrogen (N$_2$) at 538° C. to decompose and remove the organic template. The N$_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C. After air calcination, properties of the resulting catalyst were: Alpha Value=500; hexane sorption: 53.8 mg/g; BET surface area, total(micro+meso) of 479/(312+168) m$^2$/g; and mesopore volume=0.427 cc/g.

Example 6

65/35 Meso-Mordenite/Silica Catalyst

A catalyst was made from a mixture of 65 parts (basis: calcined 538° C.) of the small meso-mordenite crystal from Example 2 and 35 parts of Ultrasil™ silica/colloidal silica (basis: calcined 538° C.) in a muller. Sufficient water was added to produce an extrudable paste on an extruder. The mixture of meso-mordenite, the silicas, and water was extruded into an extrudate, and then dried at 121° C. The crush strength of the resulting extrudates was measured and showed to be 73 lbs/in (13 kg/cm). The dried extrudate was calcined in nitrogen (N$_2$) at 538° C. to decompose and remove the organic template. The N$_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C. After air calcination, properties of the resulting catalyst were: Alpha Value=730; hexane sorption: 41.5 mg/g; BET surface area, total(micro+meso) of 446 (344+102) m$^2$/g; and mesopore volume=0.37 cc/g.

Example 7

Performance Evaluation of Examples 4 to 6

The comparative TEA-mordenite catalyst prepared in Example 4 and meso-mordenite catalysts prepared in Examples 5 and 6 were evaluated simultaneously using a high-throughput fixed-bed micro unit using a toluene and mesitylene model compound feed at 1:1 molar ratio in a process for conversion of a C$_{9+}$ aromatic hydrocarbon. One-half (0.5) g of the catalyst, sized so that length equals extrudate diameter, was loaded into a reactor. The reactors were pressurized to 300 psig and dried with flowing nitrogen (N$_2$) at 250° C. for 3 hours. After nitrogen (N$_2$) was turned off, the feed and hydrogen were introduced to each reactor at 6 WHSV and 1:1 molar ratio of H$_2$/hydrocarbon. The reactor temperature was ramped to 340° C. and kept at 340° C. for 1 hour, and the total product was analyzed by an online GC. For the rest of the experiment, the reactor temperature was increased at 10° C. per step until 450° C. was reached followed by an GC analysis at each step.

Figure 4A:
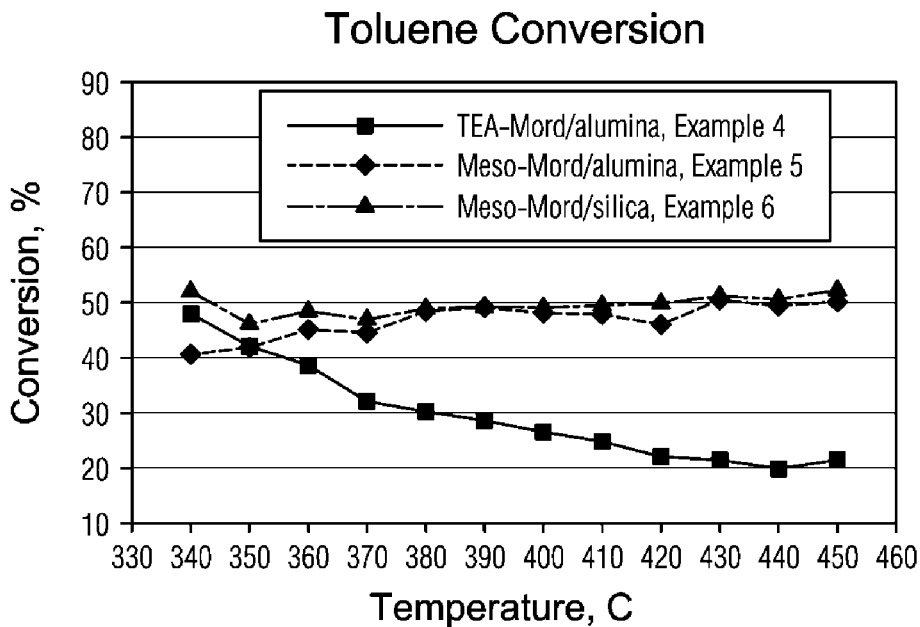
FIGS. 4A, 4B and 4C show the performance of catalysts of Examples 4, 5 and 6 using a toluene and mesitylene model feed in a process for conversion of a $C_{9+}$ aromatic hydrocarbon of Example 7.
Figure 4B:
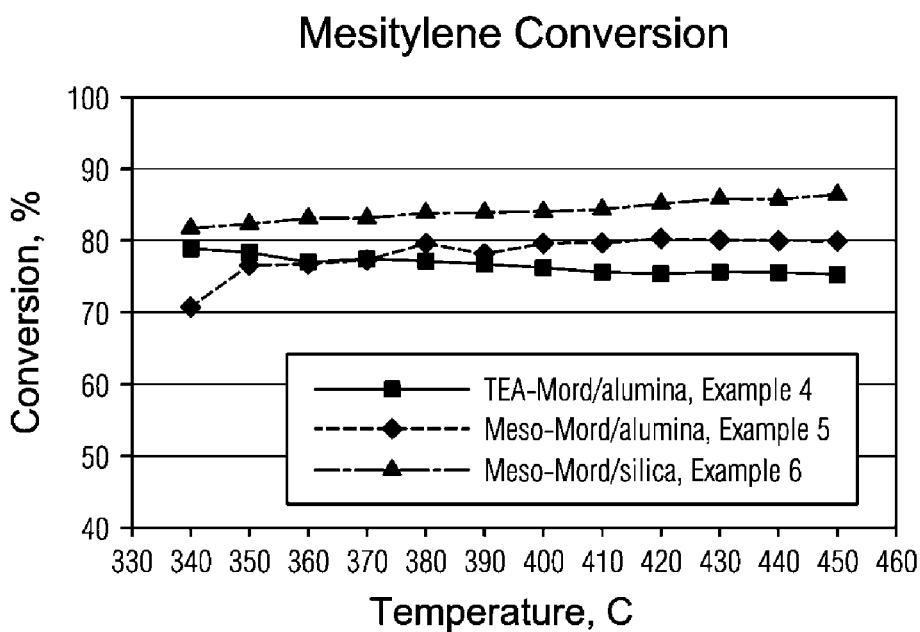
Figure 4C:
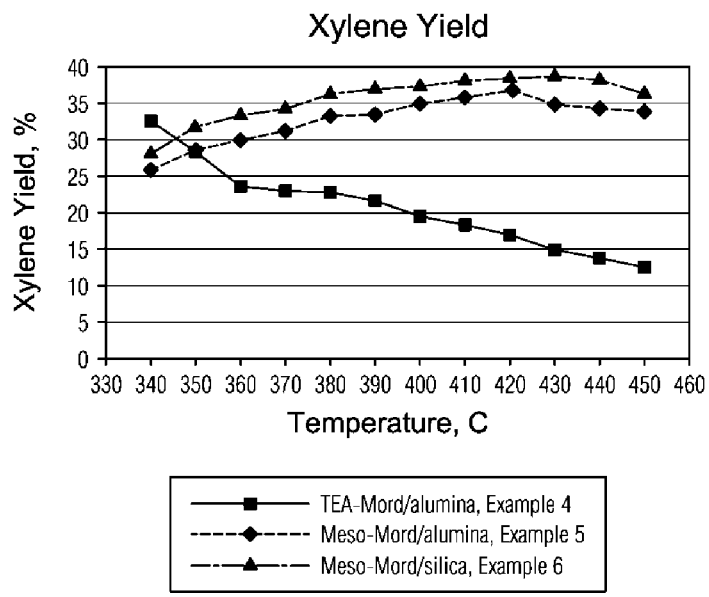

The performance data are shown in FIGS. 4A, 4B and 4C. The comparative catalyst prepared in Example 4 exhibited a decline in conversion and xylene yield with increasing temperature; whereas the meso-mordenite catalysts of Examples 5 and 6 exhibited more stable performance The meso-mordenite/silica catalyst provided the highest conversion and xylene yield in the temperature range tested.

Example 8

65/35 Meso-Mordenite/Alumina Catalyst

A catalyst was made from a mixture of 65 parts (basis: calcined 538° C.) of small meso-mordenite crystal from Example 3 and 35 parts of pseudoboehmite alumina of Versal™ 300 (obtainable from UOP LLC; basis: calcined 538° C.) in a muller. Sufficient water was added to produce an extrudable paste on an extruder. The mixture of meso-mordenite, pseudoboehmite alumina, and water was extruded into an extrudate, and then dried at 121° C. The crush strength of the resulting extrudates was measured and showed to be 136 lbs/in (24 kg/cm). The dried extrudate was calcined in nitrogen (N$_2$) at 538° C. to decompose and remove the organic template. The N$_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C. After air calcination, properties of the resulting catalyst were: Alpha Value=530; hexane sorption: 43.9 mg/g; BET surface area, total(micro+meso) of 504(336+168) m$^2$/g; and mesopore volume=0.52 cc/g.

Example 9

65/35 Meso-Mordenite/Silica Catalyst

A catalyst was made from a mixture of 65 parts (basis: calcined 538° C.) of small meso-mordenite crystals from Example 3 and 35 parts of Ultrasil™ silica/colloidal silica (basis: calcined 538° C.) in a muller. Sufficient water was added to produce an extrudable paste on an extruder. The mixture of meso-mordenite, silica, and water was extruded into an extrudate, and then dried at 121° C. The crush strength of the resulting extrudates was measured and showed to be 84 lbs/in (15 kg/cm). The dried extrudate was calcined in nitrogen (N$_2$) at 538° C. to decompose and remove the organic template. The N$_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium-exchanged extrudate was dried at 121° C. and calcined in air at 538° C. After air calcination, properties of the resulting catalyst are: Alpha Value=800; hexane sorption: 46.8 mg/g; BET surface area, total(micro+meso) of 462(360+102) m$^2$/g; Mesopore volume=0.53 cc/g.

Example 10

Performance Evaluation of Examples 6, 8 and 9

The comparative catalyst prepared in Example 4 and meso-mordenite catalysts prepared in Examples 8 and 9 were evaluated simultaneously using a high-throughput fixed-bed micro unit with the same feed and similar procedures as described in Example 7, except that the reaction temperature used was 330-400° C.

Figure 5A:
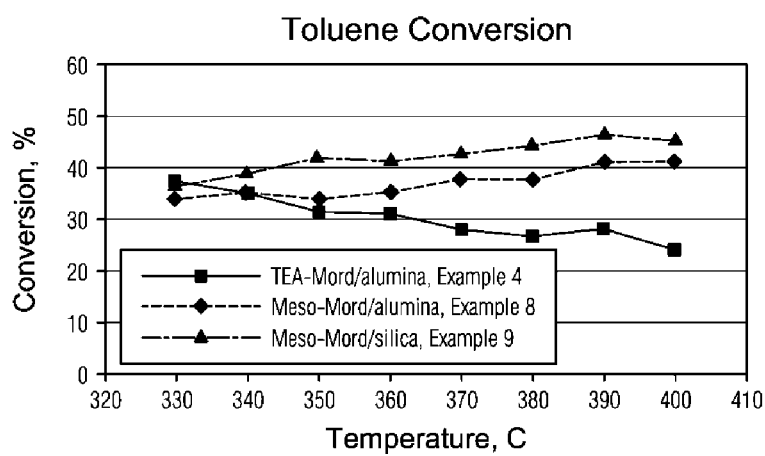
FIGS. 5A, 5B and 5C show the performance of catalysts of Examples 4, 8 and 9 using a toluene and mesitylene model feed in a process for conversion of a $C_{9+}$ aromatic hydrocarbon of Example 10.
Figure 5B:
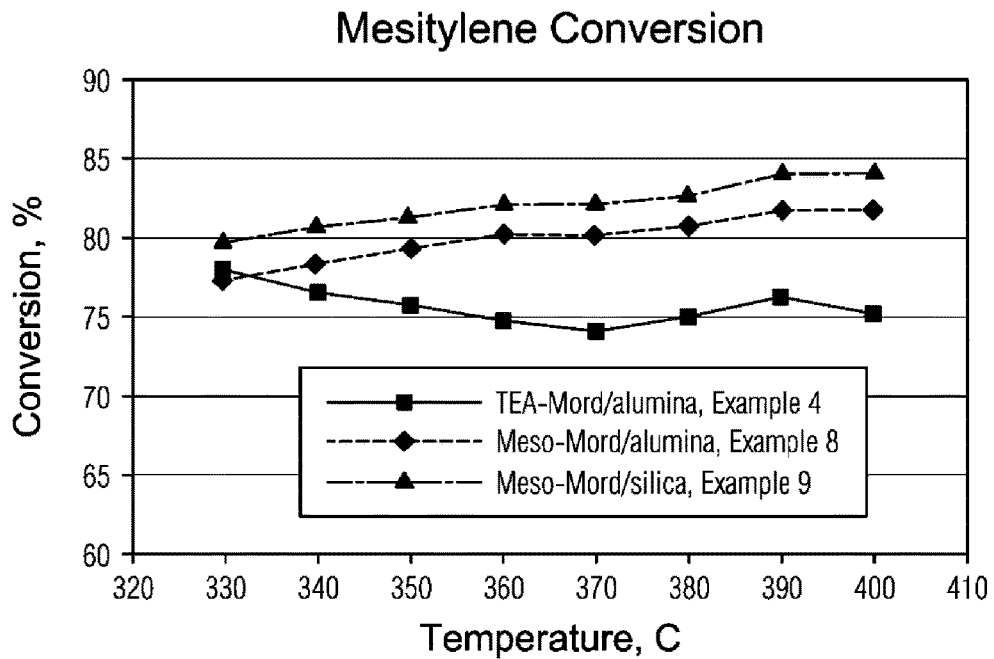
Figure 5C:
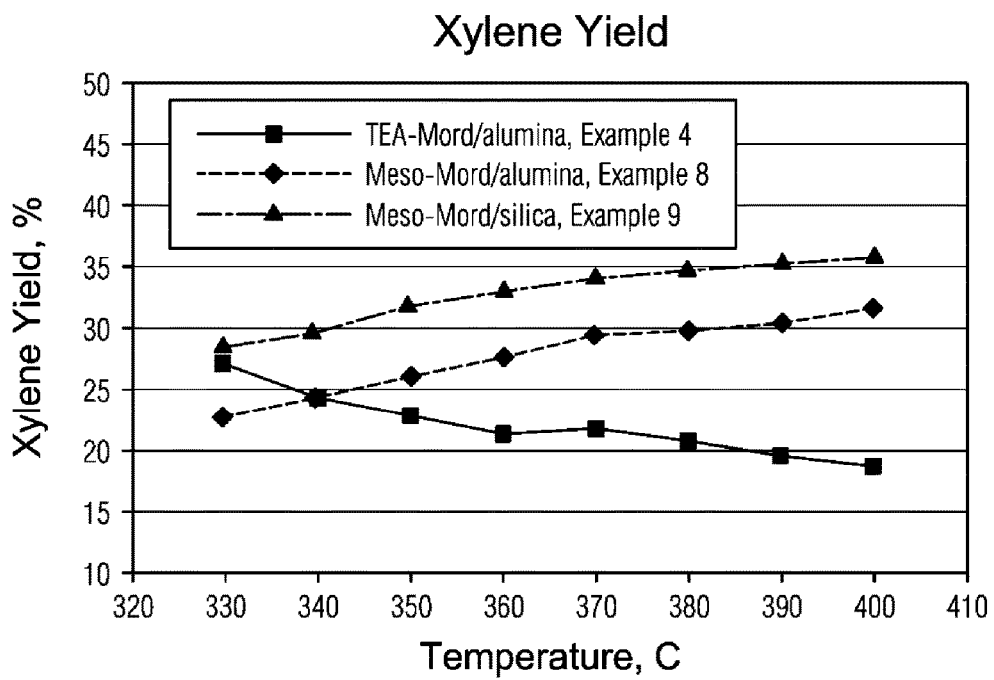

The performance data are shown in FIGS. 5A, 5B, and 5C. The comparative catalyst prepared in Example 4 exhibited a lower conversion and xylene yield with increasing temperature when compared with meso-mordenite catalysts of Examples 8 and 9. The meso-mordenite/silica catalyst of Example 9 provided highest conversion and xylene yield in the temperature range tested.

Example 11

65/35 ZSM-12 Alumina Catalyst (Comparative)

A catalyst was made from a mixture of 65 parts (basis: calcined 538° C.) of high activity ZSM-12 crystal (made according to U.S. Pat. No. 8,202,506, and referred to as "UHA-ZSM-12") and 35 parts of pseudoboehmite alumina of Versal™ 300 (basis: calcined 538° C.) in a muller. Sufficient water was added to produce an extrudable paste in an extruder.

The mixture of the high activity ZSM-12 (UHA-ZSM-12), alumina, and water was extruded into 1/20" quadrulobe and then dried at 121° C. The dried extrudate was calcined in nitrogen (N$_2$) at 482° C. to decompose and remove the organic template. The N$_2$-calcined extrudate was humidified with saturated air and exchanged with 1 N ammonium nitrate to remove sodium. After ammonium nitrate exchange, the extrudate was washed with deionized water to remove residual nitrate ions prior to drying. The ammonium exchanged extrudate was dried at 121° C. and calcined in air at 538° C. After air calcination, properties of the resulting catalyst were: Alpha=290.

Example 12

65/35 ZSM-12 Silica Catalyst (Comparative)

A catalyst was made from a mixture of 65 parts (basis: calcined 538° C.) of high activity ZSM-12 crystal (made according to U.S. Pat. No. 8,202,506, and referred to as "UHA-ZSM-12") and 35 parts of Ultrasil silica/colloidal silica (basis: calcined 538° C.) in a muller. Sufficient water was added followed by a 5% sodium hydroxide solution (targeting 0.5wt % NaOH on a 538° C. solids basis) to produce an extrudable paste on an extruder. The mixture of the high activity ZSM-12, silicas, NaOH, and water was extruded into an extrudate, and then dried at 121° C. The dried extrudate was exchanged with 1N ammonium nitrate to help remove sodium and was dried at 121° C. The dried extrudate was calcined in nitrogen (N$_2$) at 538° C. to decompose and remove the organic template. The N$_2$-calcined extrudate was humidified with saturated air and again exchanged with 1 N ammonium nitrate to remove sodium. After ammonium nitrate exchange, the extrudate was washed with deionized water to remove residual nitrate ions prior to drying. The ammonium exchanged extrudate was dried at 121° C. and calcined in air at 538° C. After air calcination, properties of the resulting catalyst were: Alpha=710; hexane sorption: 38.6 mg/g; BET Surface area, total(micro+meso) of 324/(212+112) m$^2$/g; Mesopore volume=0.51 cc/g.

Example 13

Performance Evaluation of Examples 8, 9, 11, 12

The catalysts prepared in Examples 8, 9, 11, and 12 were evaluated simultaneously using a high-throughput fixed-bed micro unit with the same feed and the same procedures described in Example 10.

Figure 6A:
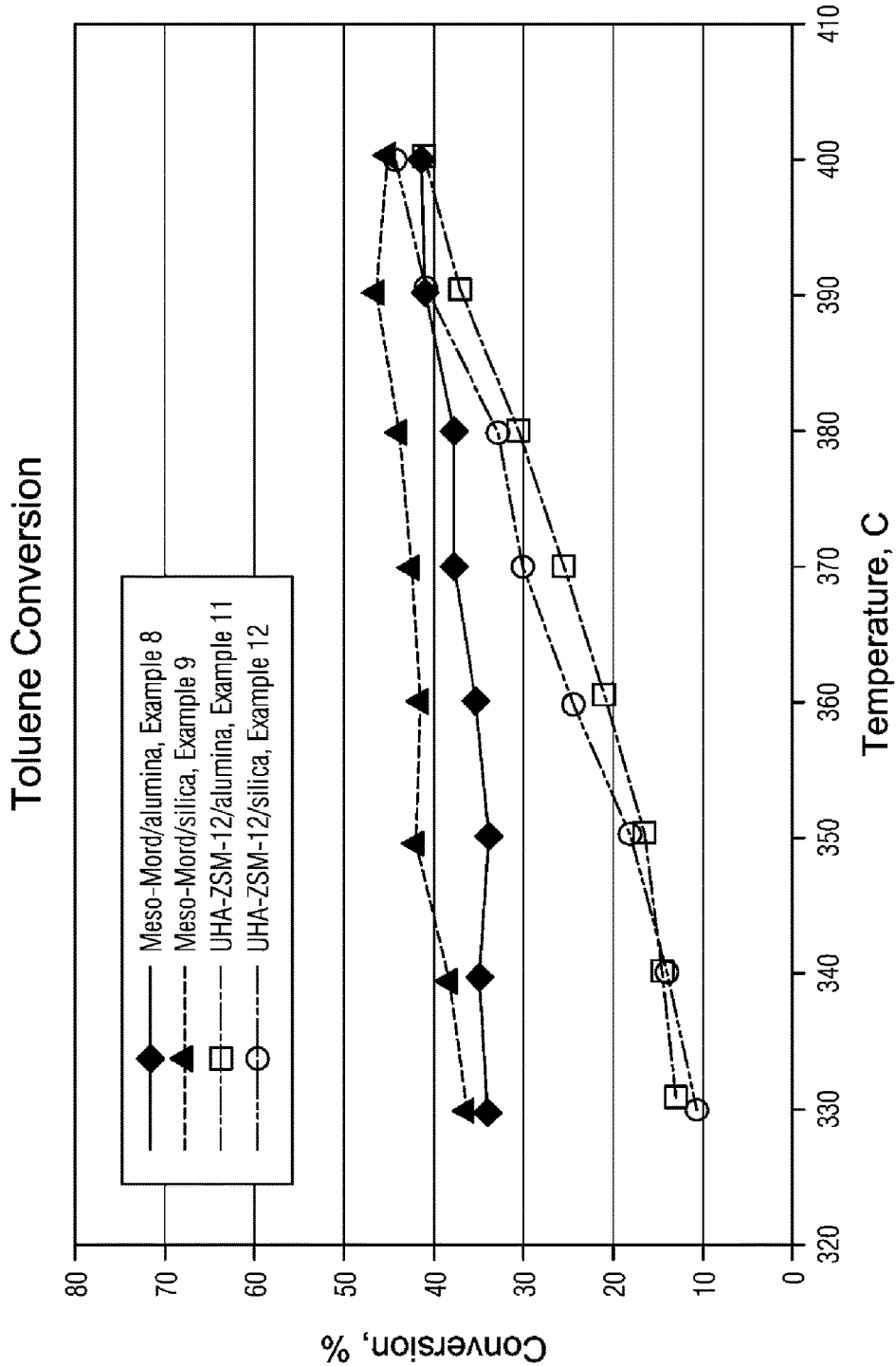
FIGS. 6A, 6B and 6C show the performance of catalysts of Examples 8, 9, 11 and 12 using a toluene and mesitylene model feed in a process for conversion of a $C_{9+}$ aromatic hydrocarbon of Example 13.
Figure 6B:
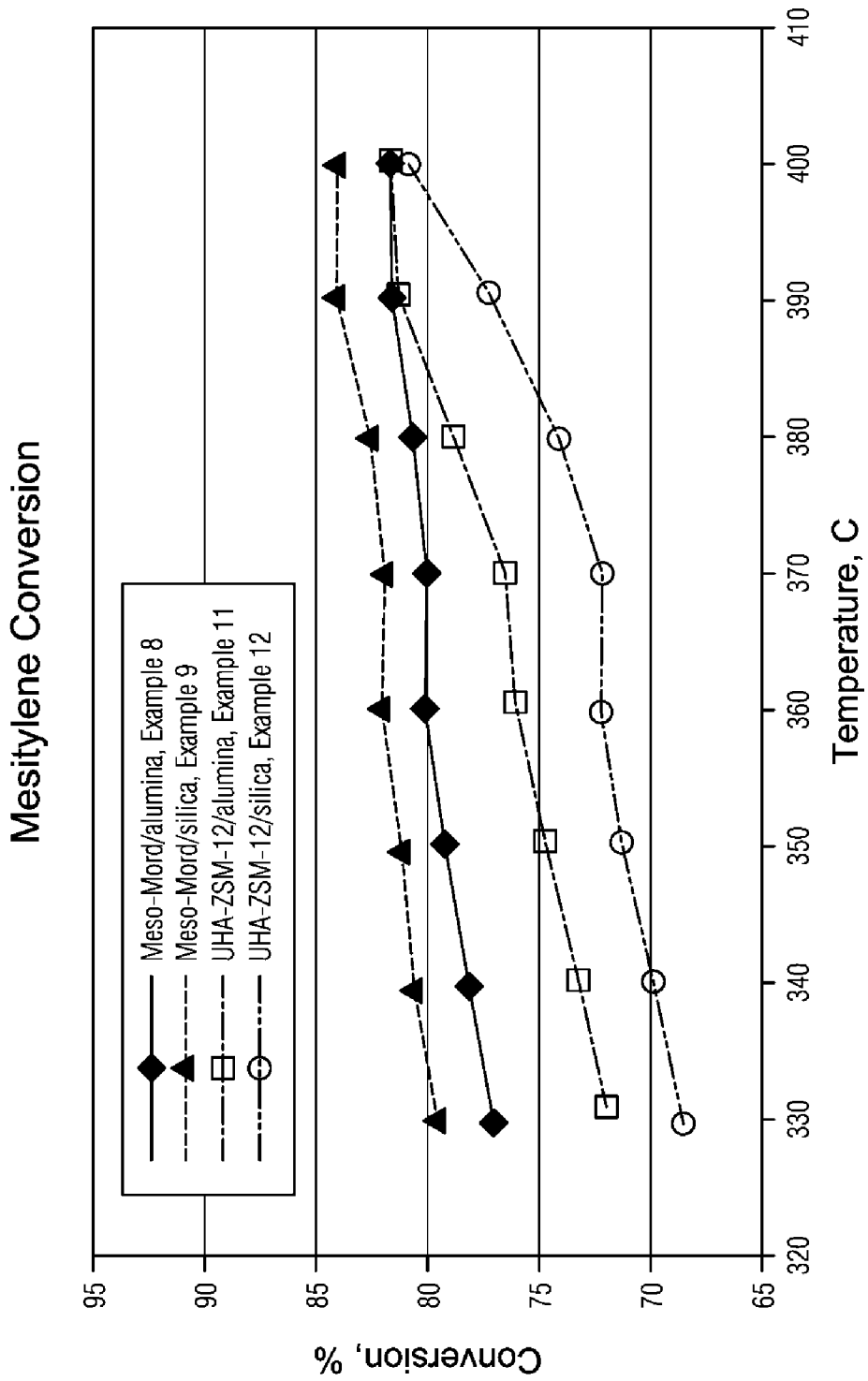
Figure 6C:
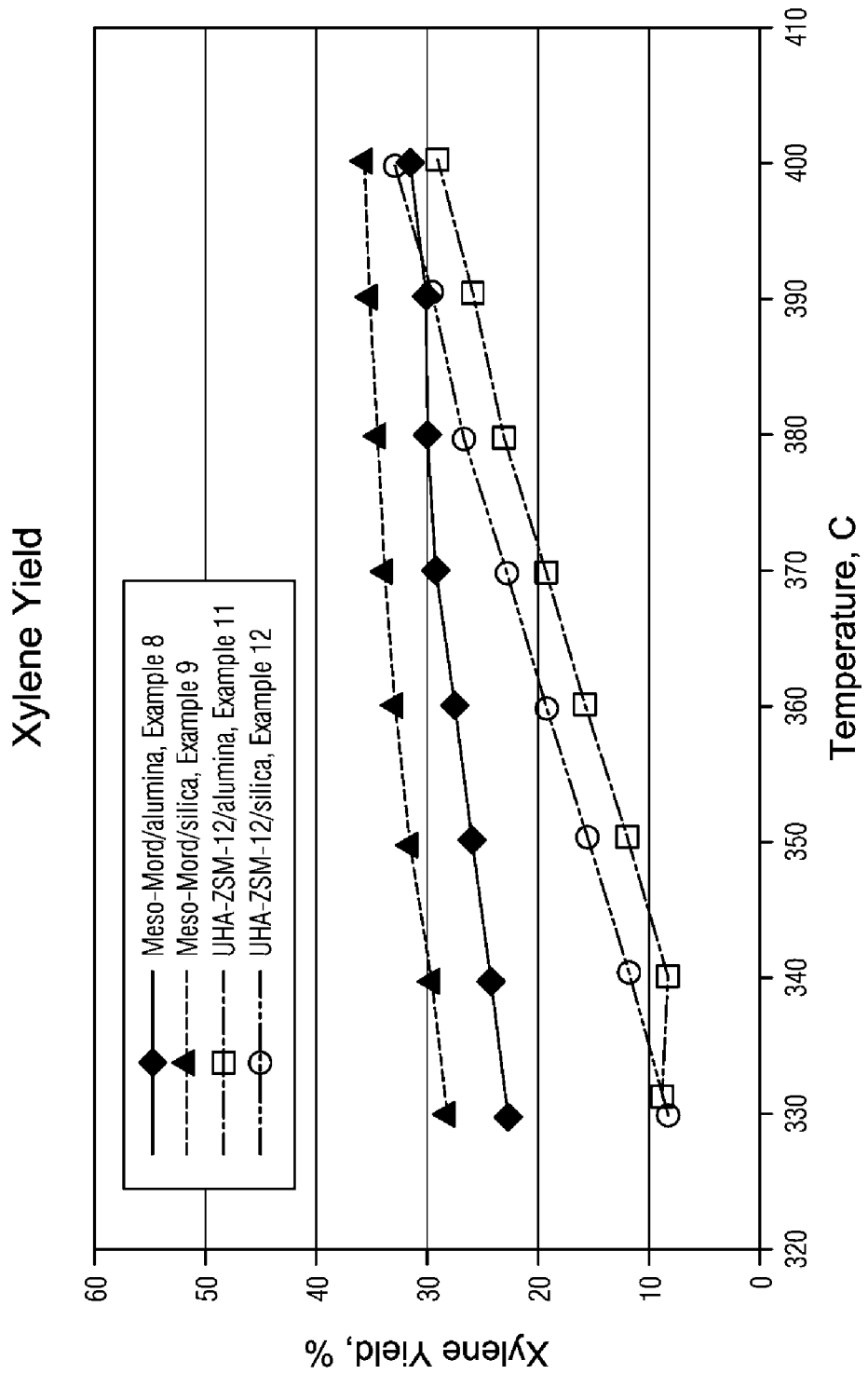

The performance data are shown in FIGS. 6A, 6B, and 6C. The meso-mordenite catalysts prepared in Examples 8 and 9 showed higher conversions and higher xylene yield when compared with the high activity ZSM-12 (UHA-ZSM-12) catalysts of Examples 11 and 12, except at 400° C. The differences between the two type of catalysts are more siginificant at lower temperatures.

Example 14

Pt/Sn on 65/35 TEA-Mordenite/Alumina Catalyst (Comparative)

The extrudate from Example 4 was co-impregnated with 0.1 wt. % Pt as tetraammonium platinum nitrate and 0.24 wt. % Sn as tin(II) chloride salt via incipient wetness. The catalyst was calcined in air at 680° F. (360° C.) for 3 hours. Characteristics of the extrudate prior to metal incorporation: Alpha=640; hexane sorption: 62 mg/g.

Example 15

Pt/Sn on Steamed 65/35 ZSM-12/Alumina Catalyst(Comparative)

0.1 wt. % Pt as tetraammonium platinum nitrate and 0.24wt. % Sn as tin(II) chloride salt were co-impregnated via incipient wetness onto a steamed extrudate of 65/35 by weight of ZSM-12/Alumina where the ZSM-12 (made according to U.S. Pat. No. 3,832,449) and having a Si/Al$_2$ molar ratio of 200/1. The extrudate was steamed for 5 hours at 900° F. (482° C.) prior to metal addition. The catalyst was calcined in air at 680° F. (360° C.) for 3 hours. Characteristics of the extrudate prior to metal incorporation: Alpha=100; hexane sorption: 37 mg/g.

Example 16

Pt/Sn on Steamed 65/35 Meso-Mordenite/Silica

The extrudate from Example 6 was steamed for 4 hours at 800° F. (427° C.) in full steam at atmospheric pressure. This steamed catalyst was co-impregnated with 0.1wt. % Pt as tetraammonium platinum nitrate and 0.24wt. % Sn as tin(II) chloride via incipient wetness. The catalyst was calcined in air at 680° F. (360° C.) for 3 hours. Characteristics of the extrudate prior to metal incorporation: Alpha=210; Hexane sorption: 20 mg/g.

Example 17

Pt/Sn on 65/35 Meso-Mordenite/Alumina Catalyst

The extrudate from Example 8 was co-impregnated with 0.1wt. % Pt as tetraammonium platinum nitrate and 0.24wt. % Sn as tin(II) chloride via incipient wetness. The catalyst was calcined in air at 680° F. (360° C.) for 3 hours. Characteristics of the extrudate prior to metal incorporation: Alpha=530; hexane sorption: 43.9 mg/g.

Example 18

Pt/Sn on 65/35 Meso-Mordenite/Alumina Catalyst

The extrudate from Example 9 was co-impregnated with 0.1wt. % Pt as tetraammonium platinum nitrate and 0.24wt. % Sn as tin(II) chloride via incipient wetness. The catalyst was calcined in air at 680° F. (360° C.) for 3 hours. Characteristics of the extrudate prior to metal incorporation: Alpha=800; hexane sorption: 46.8 mg/g.

Example 19

Performance Evaluation of Examples 14, 15, 16, 18

Examples 14, 15, 16, 17 and 18 were evaluated in a single-bed fixed bed pilot plant using a blend of 85 wt. % $C_{9+}$ as A100 Fluid and 15 wt. % toluene. The feed blend is identified as "Feed Blend #1" or "Feed Blend #2". Performance of a reference catalyst system shifted depending upon the feed blend used.

Therefore, only catalysts run on the same feed blend can be compared. Feed data for both blends are provided in Table 2, below.

TABLE 2

| Component | Feed Blend #1 | Feed Blend #2 |
|---|---|---|
| Benzene | 0.00 | 0.01 |
| Toluene | 15.42 | 15.07 |
| Ethylbenzene | 0.00 | 0.00 |
| o-Xylene | 0.05 | 0.12 |
| m-Xylene | 0.00 | 0.00 |
| Other $C_9$ Paraffins | 0.04 | 0.11 |
| n-Propylbenzene | 3.18 | 2.13 |
| Isopropylbenzene | 1.01 | 0.52 |
| 1-Methyl-2-Ethylbenzene | 5.59 | 4.66 |
| 1-methyl-3-Ethylbenzene | 13.76 | 11.45 |
| 1-Methyl-4-Ethylbenzene | 6.76 | 4.92 |
| 1,2,3-Trimethylbenzene | 5.75 | 6.45 |
| 1,2,4-Trimethylbenzene | 28.57 | 32.86 |
| 1,3,5-Trimethylbenzene | 8.27 | 10.09 |
| Indane | 0.74 | 0.78 |
| Other $C_{10}$ Paraffins | 1.33 | |
| 1-Methyl-3-n-Propylbenzene | 1.03 | 1.06 |
| 1-Methyl-4-n-Propylbenzene | 0.40 | 0.42 |
| 1-Methyl-3-Isopropylbenzene | 0.46 | |
| 1-Methyl-4-Isopropylbenzene | 0.15 | 0.16 |
| 1,2-Diethylbenzene | 0.09 | 0.09 |
| 1,3-Diethylbenzene | 0.61 | 0.58 |
| 1,4-Diethylbenzene | 0.23 | 0.20 |
| 1,2-Dimethyl-3-Ethylbenzene | 0.24 | 0.24 |
| 1,2-Dimethyl-4-Ethylbenzene | 1.52 | 0.93 |
| 1,3-Dimethyl-2-Ethylbenzene | 0.09 | 0.07 |
| 1,3-Dimethyl-4-Ethylbenzene | 0.86 | 1.62 |
| 1,3-Dimethyl-5-Ethylbenzene | 1.84 | 2.05 |
| 1,4-Dimethyl-2-Ethylbenzene | 0.00 | 1.07 |
| 1,2,3,4-Tetramethylbenzene | 0.14 | 0.14 |
| 1,2,3,5-Tetramethylbenzene | 0.77 | 0.81 |
| 1,2,4,5-Tetramethylbenzene | 0.61 | 0.64 |
| Naphthalene | 0.05 | 0.05 |
| m-Indanes | 0.06 | 0.09 |
| Other $C_{10}$ Aromatics | 0.31 | 0.59 |
| 1-Methyl-Naphthalene | 0.00 | 0.00 |
| 2-Methyl-Naphthalene | 0.00 | 0.00 |
| Other C11 Aromatics | 0.05 | 0.01 |
| Total | 100.00 | 100.0 |

The amount of 3.4 grams of the catalyst was loaded into the reactor. The catalyst was heated in hydrogen and activated at 752° F. (400° C.) for 1 hour. The temperature was then increased to 806° F. (430° C.) and liquid feed was introduced for a 12 hour de-edging period. Following the de-edging period, conditions were modified to evaluate catalyst performance. Conditions of the de-edging and subsequent reaction conditions were:

De-edging Conditions: WHSV=4.4 $hr^{-1}$, $H_2$/HC=1, temperature=806° F. (430° C.) for 12 hours, and pressure=350 psig (2413 kPa). Temperature Scan Conditions:

WHSV=4.4 $hr^{-1}$, $H_2$/HC=2, temperature=734° F. (390° C.), and pressure=350 psig (2413 kPa).

The product was analyzed by on-line GC. Performance comparisons can be found in Table 3, below.

TABLE 3

| Example | Description | Feed Blend # | Ethyl-Aromatic Conversion at 734° F. (390° C.) | $C_{9+}$ Conversion at 734° F. (390° C.) | % Xylenes at 734° F. (390° C.) |
|---|---|---|---|---|---|
| 14 | Pt/Sn on TEA-Mordenite/Alumina | 3 | 54 | 43 | 25 |
| 15 | Pt/Sn on Steamed ZSM-12/Alumina | 2 | 21 | 30 | 19 |
| 16 | Pt/Sn on Steamed Meso-Mordenite/Silica | 2 | 50 | 49 | 27 |
| 17 | Pt/Sn on Meso-Mordenite/Alumina | 3 | 58 | 44 | 29 |
| 18 | Pt/Sn on Meso-Mordenite/Silica | 3 | 64 | 47 | 31 |

Comparing the performance of Examples 14, 17, and 18 using Feed Blend #1 in Table 3 exhibits the benefit in performance of the meso-mordenite zeolite over a more traditional version of Mordenite, TEA-Mordenite. Both transalkylation and de-alkylation activity are higher for the meso-mordenite (a higher activity-Mordenite). As a result, xylene yields are dramatically higher for the meso-mordenite catalyst over the TEA-mordenite based catalyst.

Comparing the performance of Example 15 and 16 using Feed Blend #2 in Table 3 exhibits the benefit of meso-mordenite zeolite over ZSM-12. The meso-mordenite shows significantly higher de-ethylation activity and transalkylation activity as evidenced by the higher xylene yield.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention claimed is:

1. A process, comprising:
   contacting a feedstock comprising toluene, $C_{8+}$ aromatic hydrocarbons and optionally hydrogen with a catalyst under suitable conversion conditions to transalkylate the $C_{8+}$ aromatic hydrocarbons with toluene; and
   producing an effluent stream comprising aromatic products that are lighter than at least some of the $C_{8+}$ aromatic hydrocarbons in the feedstock, wherein the aromatic products comprise xylenes, wherein the catalyst composition comprises a mordenite zeolite synthesized from TEA or MTEA, wherein the mordenite zeolite has a mesopore surface area of greater than 30 m$^2$/g and the mordenite comprises agglomerates composed of primary crystallites, and wherein the primary crystallites have an average primary crystal size as measured by TEM of less than 80 nm and an aspect ratio of less than 2.

2. The process of claim 1, wherein the catalyst further comprises (ii) 0.005 to 5.0 wt. % of at least one first metal of Group 10 of the IUPAC Periodic Table, based on the weight of the catalyst composition.

3. The process of claim 2, wherein the catalyst further comprises (iii) 0.01 to 5.0 wt. % of at least one a second metal of Group 11 to 15 of the IUPAC Periodic Table, based on the weight of the catalyst composition.

4. The process of claim 1, wherein the $C_{8+}$ aromatic hydrocarbons of the feedstock comprise aromatic compounds having nine or more carbon atoms.

5. The process of claim 1, wherein the feedstock further comprises benzene.

6. The process of claim 1, wherein the $C_{8+}$ aromatic hydrocarbons comprises aromatic compounds having a boiling point in the range of 135° C. to 260° C. at atmospheric pressure.

7. The process of claim 1, wherein the effluent stream comprises at least one selected from the group consisting of benzene, and toluene.

8. The process of claim 1, wherein the suitable conversion conditions comprise a temperature of 340° C. to 515° C., a pressure from 380 kPa (55 psia) to 4240 kPa (615 psia) and a weight hourly space velocity (WHSV) in the range of 1 to 100 hr$^{-1}$ based on the weight of the feedstock.

9. The process of claim 1, further comprising a reactor for contacting said feedstock with the catalyst composition under the suitable conversion conditions, wherein the reactor comprises at least one fixed catalyst bed of the catalyst composition.

10. The process of claim 1, further comprising a reactor for contacting feedstock with the catalyst composition under the suitable conversion conditions, wherein the reactor comprises at least one fluid bed of the catalyst composition.

* * * * *